United States Patent
Son et al.

(10) Patent No.: US 12,122,813 B2
(45) Date of Patent: Oct. 22, 2024

(54) FUSION PROTEIN COMPRISING AN ANTIGEN BINDING DOMAIN AND A CYTOKINE TRIMER DOMAIN

(71) Applicant: CTCELLS, INC., Daegu (KR)

(72) Inventors: Kka Bi Son, Daejeon (KR); Jeong Hyeon Bak, Daejeon (KR); Dae Hee Lee, Daejeon (KR); Se Il Jang, Daejeon (KR); Jung Min Lee, Daegu (KR); Ji Hye Yoon, Daejeon (KR); Jong Gwan Jeong, Daejeon (KR)

(73) Assignee: CTCELLS, INC., Daegu (KR)

( * ) Notice: Subject to any disclaimer, the term of this patent is extended or adjusted under 35 U.S.C. 154(b) by 0 days.

(21) Appl. No.: 18/041,845

(22) PCT Filed: Jun. 22, 2022

(86) PCT No.: PCT/KR2022/008883
§ 371 (c)(1),
(2) Date: Feb. 16, 2023

(87) PCT Pub. No.: WO2023/158027
PCT Pub. Date: Aug. 24, 2023

(65) Prior Publication Data
US 2023/0272026 A1     Aug. 31, 2023

(30) Foreign Application Priority Data

Feb. 21, 2022  (KR) .......... 10-2022-0022526
Apr. 15, 2022  (KR) .......... 10-2022-0046740

(51) Int. Cl.
*C07K 14/52*     (2006.01)
*C07K 14/525*    (2006.01)
*C07K 16/18*     (2006.01)
*C07K 16/28*     (2006.01)
*C07K 19/00*     (2006.01)

(52) U.S. Cl.
CPC ........... *C07K 14/525* (2013.01); *C07K 16/18* (2013.01); *C07K 16/28* (2013.01); *C07K 16/2878* (2013.01); *C07K 19/00* (2013.01); *C07K 2319/00* (2013.01); *C07K 2319/30* (2013.01); *C07K 2319/70* (2013.01)

(58) Field of Classification Search
CPC .. C07K 2319/00; C07K 14/52; C07K 14/521; C07K 14/525; C07K 19/00; C07K 16/18; C07K 16/28; C07K 2319/70
See application file for complete search history.

(56) References Cited

U.S. PATENT DOCUMENTS

| 2012/0244112 A1* | 9/2012 | Ast ................. C07K 16/30 |
| | | 536/23.4 |
| 2020/0270321 A1 | 8/2020 | Amann et al. |
| 2020/0291089 A1 | 9/2020 | Loew et al. |

FOREIGN PATENT DOCUMENTS

| WO | 2019/086499 A1 | 5/2019 |
| WO | 2020/260329 A1 | 12/2020 |

OTHER PUBLICATIONS

Arai et al. Cytokines: Coordinators of immune and inflammatory responses. Annu Rev Biochem 59: 783-836, 1990.*
Bhattacharya et al. Impact of genetic variation on three dimensional structure and function of proteins. PLoS One 12(3): e0171355, 2017.*
Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
Doerks et al. Protein annotation: detective work for function prediction. Trends in Genetics 14:248-250, 1998.*
Fenton et al. Rheostat positions: a new classification of protein positions relevant to pharmacogenomics. Medicinal Chem Res 29: 1133-1146, 2020.*
Guo et al. Protein tolerance to random amino acid change. Proc Natl Acad Sci USA 101(25): 9205-9210, 2004.*
Kelso, A. Cytokines: Principles and prospects. Immunol Cell Biol 76: 300-317, 1998.*
Ngo et al. "Computational complexity, protein structure prediction, and the Levinthal paradox" in The Protein Folding Problem and Tertiary Structure Prediction, pp. 492-495, 1994.*
Ridgway et al. 'Knobs-into-holes' engineering of antibody CH3 domains for heavy chain heterodimerization. Protein Engineer 9(7): 617-621, 1996.*
Skolnick et al. From genes to protein structure and function: novel applications of computational approaches in the genomic era. Trends Biotechnol 18(I):34-39 2000.*

(Continued)

*Primary Examiner* — Bridget E Bunner
(74) *Attorney, Agent, or Firm* — SALIWANCHIK, LLOYD & EISENSCHENK

(57) ABSTRACT

The present invention relates to a cytokine trimer domain in which a first monomer and a second monomer linked by linker (dimer) and a third monomer are coupled by a knob-into-hole and a novel type of fusion protein in which antibody and cytokine trimer domains are linked (receptor-antibody conjugated (cell) engager, RACE) prepared by replacing a constant region (Fc) of an antibody with the cytokine trimer domain, and RACE according to the present invention exhibits superior binding ability to the target receptor than the parent antibody as well as excellent simultaneous binding ability to the antigen and the target receptor, which can be usefully utilized as a bispecific pharmaceutical composition.

22 Claims, 18 Drawing Sheets
Specification includes a Sequence Listing.

(56) References Cited

OTHER PUBLICATIONS

Smith et al. The challenges of genome sequence annotation or "the devil is in the details". Nature Biotechnol 15: 1222-1223, 1997.*
Tokuriki et al. Stability effects of mutations and protein evolvability. Curr Opin Structural Biol 19: 596-604, 2009.*
Turner et al. Cytokines and chemokines: At the crossroads of cell signalling and inflammatory disease. Biochim Biophys Acta 1843: 2563-2582, 2014.*
Wells, J.A. Additivity of mutational effects in proteins. Biochemistry 29(37): 8509-8517, 1990.*
Ridgway (Year: 1996).*
Bodmer et al. The molecular architecture of the TNF superfamily. Trends Biochem Sci 27(1): 19-26, 2002.*
Written Opinion dated Nov. 14, 2022 in International Application No. PCT/KR2022/008883.
Aschmoneit, N. et al., "Fc-based Duokines: dual-acting costimulatory molecules comprising TNFSF ligands in the single-chain format fused to a heterodimerizing Fc (scDk-Fc)," Oncoimmunology, 2022, 11(1):1-13.
Fellermeier, S. et al., "Advancing targeted co-stimulation with antibody-fusion proteins by introducing TNF superfamily members in a single-chain format," Oncoimmunology, 2016, 5(11):1-12.

\* cited by examiner

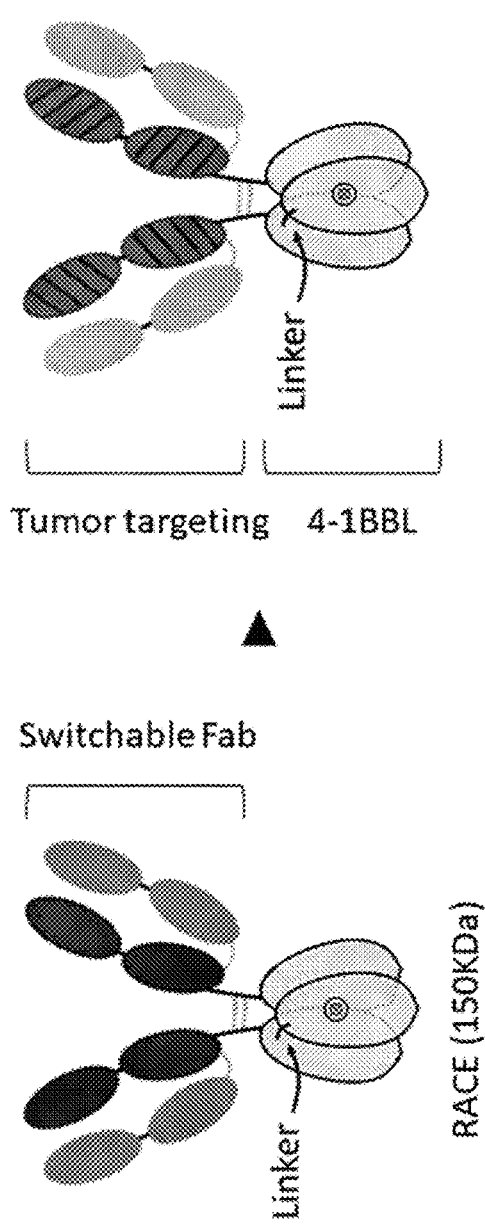
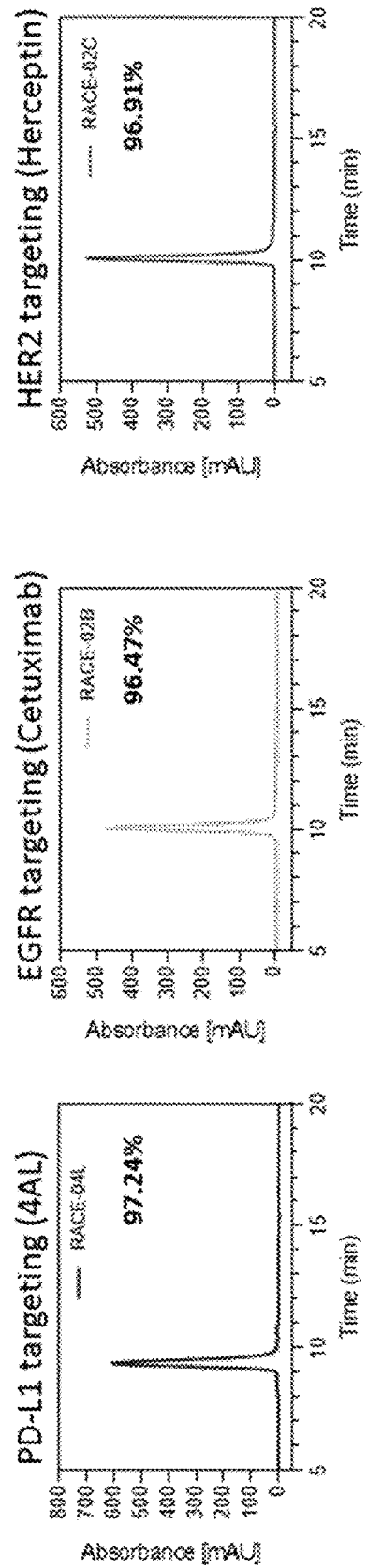
Fig.5

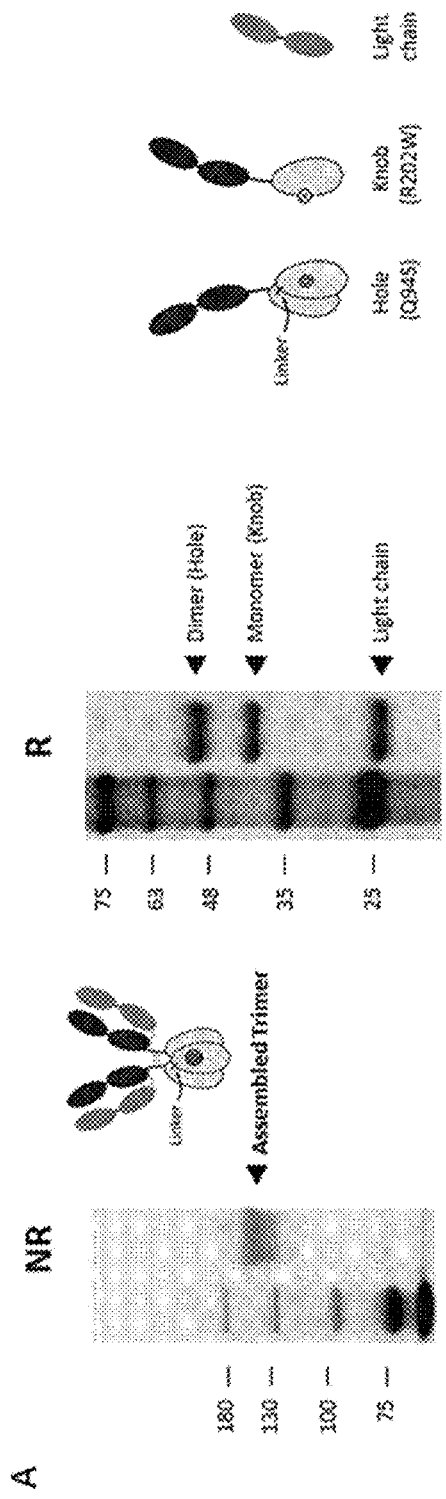
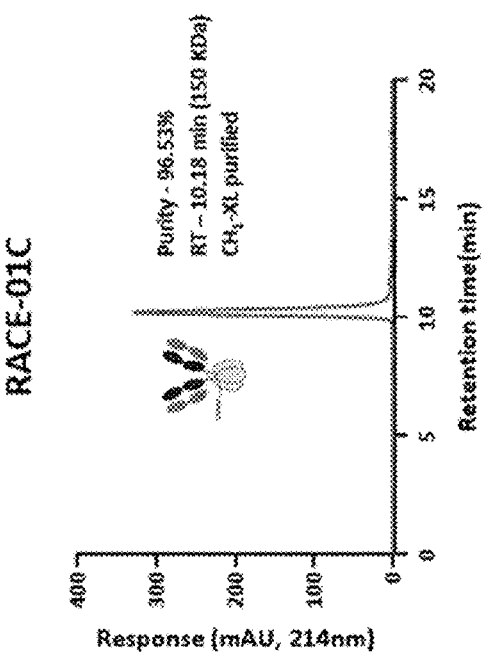
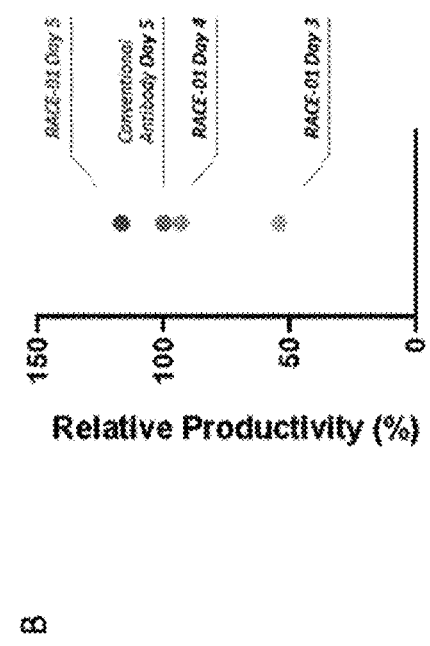
Fig. 6A
Fig. 6B
Fig. 6C
Designed RACE assembly

Fig.10
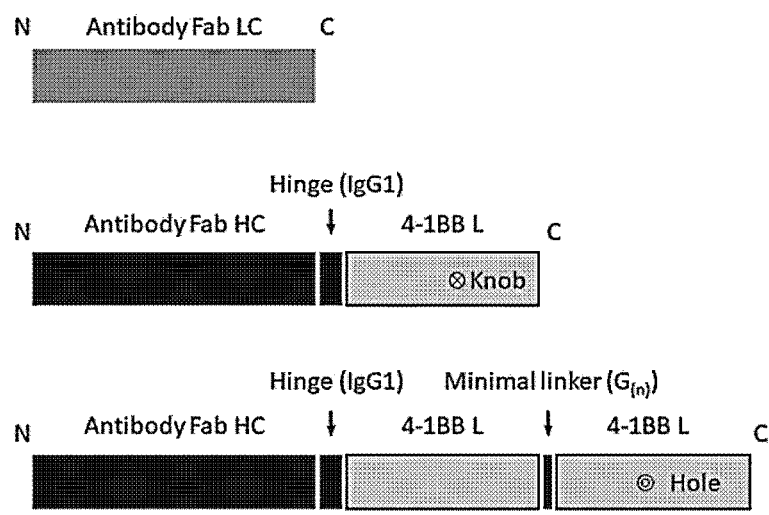
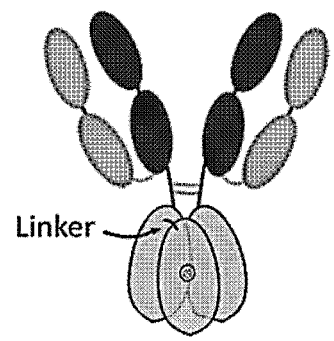

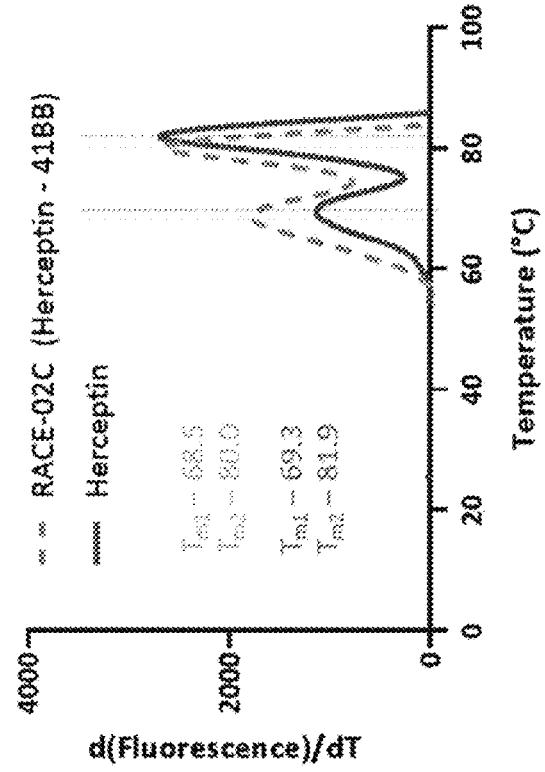
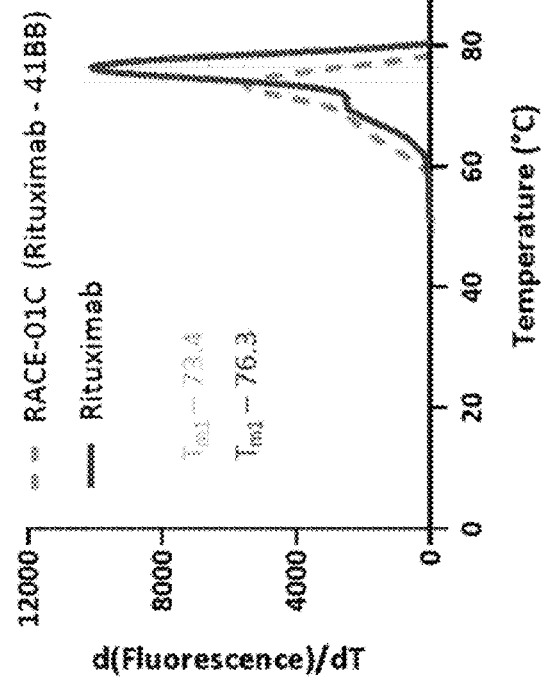
Fig.11
Stability of RACE platform as an alternative for Fc Target specific binding of RACE – Tumor targeting (SPR)

Fig.13
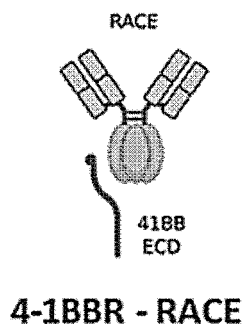
4-1BBR - RACE
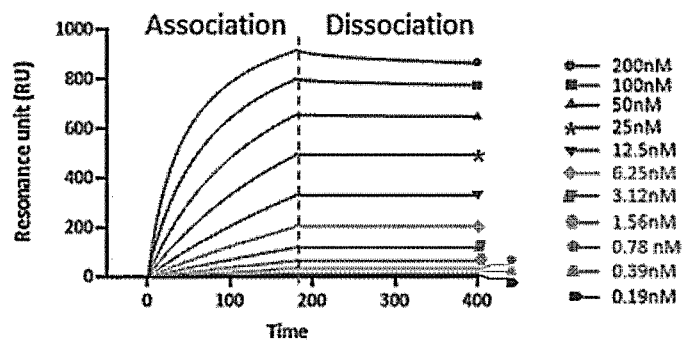
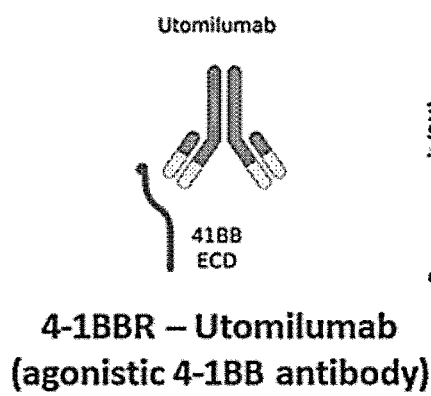
**4-1BBR – Utomilumab
(agonistic 4-1BB antibody)**
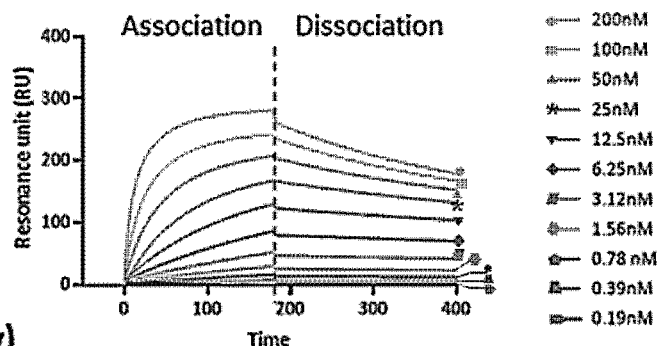
Target specific binding of RACE – CD137 binding (SPR)

Simultaneous target binding of RACE (SPR)

Fig.15
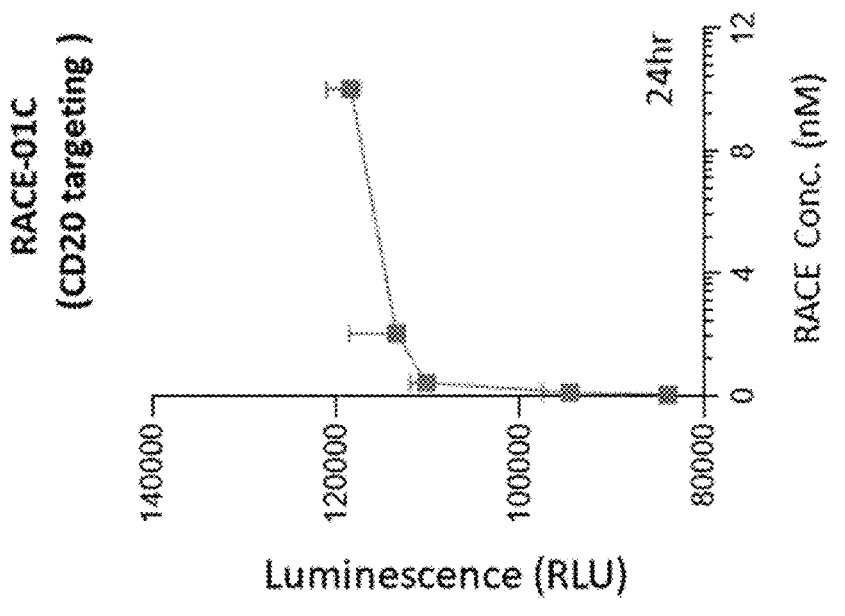
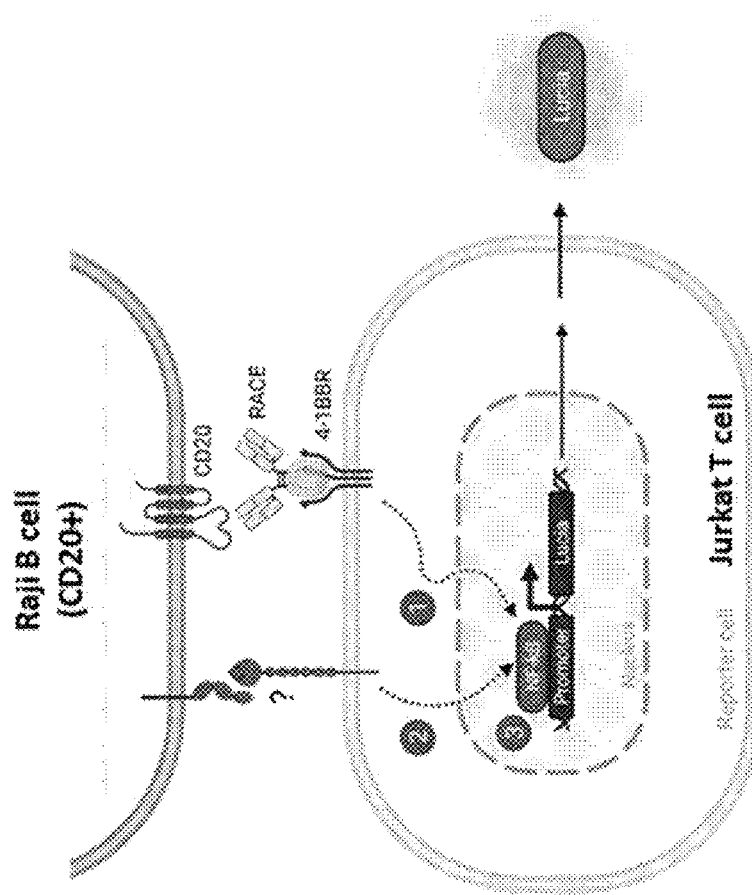
41BB reporter activity in hematological tumor

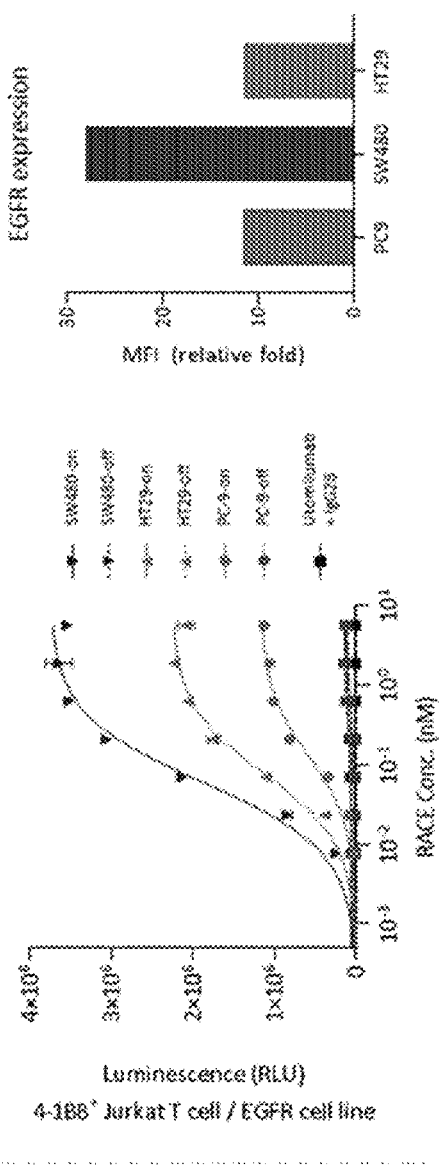
Fig. 16A
Fig. 16B
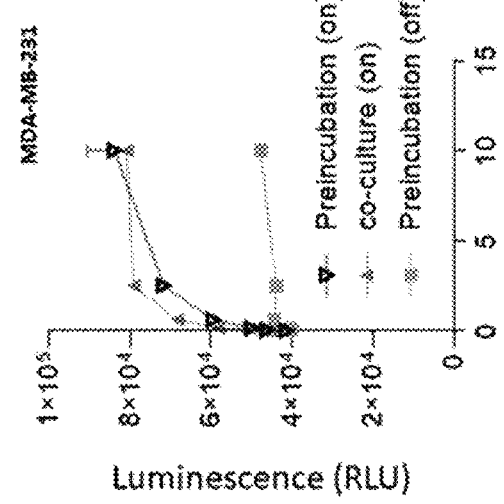
41BB reporter activity in solid tumor

FUSION PROTEIN COMPRISING AN ANTIGEN BINDING DOMAIN AND A CYTOKINE TRIMER DOMAIN

CROSS-REFERENCE TO RELATED APPLICATIONS

This application is the U.S. national stage application of International Patent Application No. PCT/KR2022/008883, filed Jun. 22, 2022, which claims the benefit under 35 U.S.C. § 119 of Korean Application Nos. 10-2022-0022526, filed Feb. 21, 2022; and 10-2022-0046740, filed Apr. 15, 2022; the disclosures of each of which are incorporated herein by reference in their entirety.

REFERENCE TO SEQUENCE LISTING

The Sequence Listing for this application is labeled "SeqList-18Apr24 ST25" which was created on Apr. 18, 2024 and is 34,796 bytes. The entire content of the sequence listing is incorporated herein by reference in its entirety.

TECHNICAL FIELD

The present invention relates to a fusion protein including an antigen binding domain and a cytokine trimer domain, a method for producing the same, and a use thereof.

BACKGROUND ART

The CD19/CD3 linker blinatumomab (Blincyto, Amgen), which was designed using an anti-CD19 antibody and an anti-CD3 antibody, was approved to accelerate the development of bispecific antineoplastic agents that induces tumor treatment through homing of immune cells.

The anti-CD3 antibody mainly targets the CD3 epsilon (CD3e) molecule present on the interface of T cells, induces T cell activation, and targets cells expressing the target antigen bound by the bispecific antibody to induce apoptosis. In the case of such a CD3 targeting bispecific antibody, it rapidly promotes T cell activity within a short period of time to accelerate target cell death, and in this process, it sometimes induces rapid secretion of cytokines. This is believed to be due to the essential properties of the CD3 molecule, which resides on the T cell interface to induce the primary activity of the cell.

The activity of immune cells, including T cells, is regulated by a balance between costimulatory and inhibitory factors. Costimulatory factors that help the activity of immune cells are largely divided into two types of the protein family, which include B7 receptor family proteins including CD28 and ICOS (Inducible Costimulatory Molecule), and TNF receptor proteins including 4-1BB and OX40. In particular, these costimulatory factor proteins are well known as inducible molecules expressed in activated T cells, and it is believed that these costimulatory factor proteins may alleviate the problem related to toxicity of the CD3 antibody.

It is known that the 4-1BB ligand (CD137L) is expressed in antigen-presenting cells to signal transduction to the 4-1BB receptor. 4-1BB ligand exists in two forms: a membrane protein form that is embedded in the cell membrane and a water-soluble form with the top of the membrane-binding site cut off. Water-soluble 4-1BB ligand does not contribute to signal transduction of 4-1BB receptor, whereas the membrane protein 4-1BB ligand strongly induces the activation of 4-1BB receptor-expressing T cells or NK cells. Through this, it has been reported that the promotion of 4-1BB signaling can inhibit tumor growth. Accordingly, various types of antibody molecules capable of functionally activating 4-1BB have been developed for the purpose of treating tumors.

Interestingly, active antibodies that inhibit the binding of 4-1BB ligand and 4-1BB receptor and help the aggregation of the 4-1BB receptor (e.g., Utomilumab, Pfizer) do not have sufficient activity alone. However, it was observed to have some activity when bound to Fc-receptors. On the other hand, active antibodies that help the aggregation of the 4-1BB receptor and ligand complex by additional binding while the 4-1BB ligand and the 4-1BB receptor are bound (e.g., Urelumab, BMS-663513, BMS) have sufficient activity without the aid of the Fc-receptor but exhibits strong toxicity due to the Fc-receptor in the body. In fact, clinical trials of Urelumab were discontinued due to such liver toxicity (NCT00612664).

In addition to this, there have been attempts to design molecules with tumor-inhibitory effect using the 4-1BB ligand itself, but no significant results have been achieved in a bivalent molecular design in which it may maintain the intrinsic structure of the ligand with minimal changes and can act specifically for tumors.

DISCLOSURE

Technical Problem

The present inventors have developed a cytokine trimer domain while studying the molecular design which maintains the intrinsic structure of the ligand and acts in a tumor-specific manner. In particular, they have derived a method for preparing a fusion protein including a cytokine trimer domain linked to the antigen binding domain in a knob-into-hole structure and confirmed the binding ability of the fusion protein prepared by this method to each target, thereby completing the present invention.

Accordingly, a purpose of the present disclosure is to provide a fusion protein.

Another purpose of the present disclosure is to provide a polynucleotide encoding a fusion protein.

Another purpose of the present disclosure is to provide a vector including a polynucleotide encoding a fusion protein.

Another purpose of the present disclosure is to provide a vector including a polynucleotide encoding a fusion protein.

Another purpose of the present disclosure is to provide a method for producing a fusion protein.

Another purpose of the present disclosure is to provide a method for producing an antibody and a tumor necrosis factor superfamily trimeric fusion protein.

Another purpose of the present disclosure is to provide a pharmaceutical composition for inhibiting or treating a disease caused by the inactivation of immune cells.

Another purpose of the present disclosure is to provide a method for treating a disease caused by the inactivation of immune cells.

Technical Solution

In order to achieve the above purpose, the present invention provides a fusion protein including an antigen binding domain and a cytokine trimer domain.

In order to achieve the above another purpose, the present invention provides a polynucleotide encoding a fusion protein according to the present invention.

In order to achieve the above another purpose, the present invention provides a vector including a polynucleotide encoding a fusion protein according to the present invention.

Further, the present invention provides a vector composition for producing the fusion protein, the composition including: a first vector in which a polynucleotide encoding the heavy chain of the Fab is operably linked to a polynucleotide encoding a first monomer and a second monomer linked by a linker; a second vector in which a polynucleotide encoding the heavy chain of the Fab is operably linked to a polynucleotide encoding a third monomer; and a third vector including a polynucleotide encoding the light chain of the Fab.

In order to achieve the above another purpose, the present invention provides a method for producing a fusion protein, the method including a step of infecting a host cell with a vector including a polynucleotide encoding the fusion protein according to the present invention.

Further, the present invention provides a method for producing a fusion protein, the method including a step of infecting a host cell with the vector composition for producing the fusion protein of claim 1, the composition including: a first vector in which a polynucleotide encoding the heavy chain of the Fab is operably linked to a polynucleotide encoding a first monomer and a second monomer linked by a linker; a second vector in which a polynucleotide encoding the heavy chain of the Fab is operably linked to a polynucleotide encoding a third monomer; and a third vector including a polynucleotide encoding the light chain of the Fab.

In order to achieve the above another purpose, the present invention provides a method for producing antibody and tumor necrosis factor superfamily (TNFSF) trimeric fusion protein, in which the tumor necrosis factor superfamily forms a trimer including a dimer including a first and second monomers of the tumor necrosis factor superfamily; and a third monomer of the tumor necrosis factor superfamily, the method including steps: 1) selecting one of the two interfaces present between the dimer and the third monomer; 2) selecting an amino acid pair located at a distance of 6 Å or less between the first or second monomer and the third monomer located at the selected first interface in the first or second monomer; and from the third monomer; 3) forming a knob by inducing a mutation in the third monomer site in the selected amino acid pair to form a knob; 4) selecting the amino acid residues of the first or second monomers of the wild type (WT) causing a steric hindrance, which are paired with the knob of the third monomer; 5) forming a hole by inducing a mutation in the amino acid residue of the selected first or second monomer; and 6) inducing a knob-into-hole interaction between the knob of the third monomer and the hole of the first or second monomer, in which the heavy chain of the Fab is linked to the dimer and the third monomer.

In order to achieve the above another purpose, the present invention provides a pharmaceutical composition for inhibiting or treating a disease caused by the inactivation of immune cells, the composition including the fusion protein according to the present invention.

In order to achieve the above another purpose, the present invention provides a method for treating a disease caused by the inactivation of immune cells, the method including a step of administering the fusion protein according to the present invention to a subject.

Advantageous Effects

The present invention relates to a cytokine trimer domain in which a first monomer and a second monomer linked by a linker (dimer) and a third monomer are coupled by a knob-into-hole and a novel type of fusion protein in which antibody and cytokine trimer domains are linked (receptor-antibody conjugated (cell) engager, RACE) prepared by replacing a constant region (Fc) of an antibody with the cytokine trimer domain, and the method for producing RACE according to the present invention increases the purity and productivity of the trimer, and RACE prepared through this exhibits the superior binding ability to the target receptor than the parent antibody as well as the excellent simultaneous binding ability to the antigen and the target receptor, which can be usefully utilized as a bispecific pharmaceutical composition.

DESCRIPTION OF DRAWINGS

FIG. 5 is a result of confirming the purity of the fusion protein including three different antibody domains and cytokine trimer domains, respectively.

FIGS. 6A-6C are results of confirming the formation of a knob-into-hole structure (FIG. 6A), production (FIG. 6B), and purity (FIG. 6C) in a fusion protein including an antibody domain and a cytokine trimer domain according to the present invention.

FIG. 10 is a result of showing the structure and size of a fusion protein including an antibody domain and a cytokine trimer domain according to the present invention.

FIG. 11 is a result of confirming the thermodynamic stability of a fusion protein including an antibody domain and a cytokine trimer according to the present invention.

FIG. 13 is a result of confirming the binding affinity of a fusion protein including an antibody domain and a cytokine trimer according to the present invention for a target receptor.

FIG. 15 is a result of evaluating the degree of 4-1BB signaling of a fusion protein including an antibody domain and a cytokine trimer according to the present invention.

FIGS. 16A and 16B are results of evaluating the degree of on-target signaling and off-target signaling of a fusion protein including an antibody domain and a cytokine trimer according to the present invention in solid cancer cell lines, which is a result for RACE-02C (FIG. 16A) and RACE-02B (FIG. 16B).

MODES OF THE INVENTION

Figure 1A:
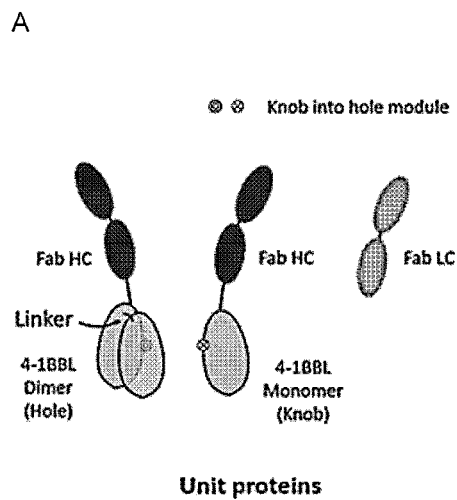
FIGS. 1A and 1B are views of showing a unit protein (FIG. 1A) and a fusion protein (FIG. 1B) including the unit protein, for the fusion protein according to the present invention.

Hereinafter, the present invention will be described in detail.

The present invention provides a fusion protein including an antigen binding domain and a cytokine trimer domain.

The cytokine trimer domain is characterized in that a dimer including a first monomer and a second monomer, and a third monomer are connected, and the dimer is characterized in that the first monomer and the second monomer are connected by a linker. The dimer is characterized in that the N or C terminus of the first monomer is interconnected with the N or C terminus of the second monomer by a linker.

Among the linkers known in the art, any linker capable of linking the first and second monomers of a cytokine may be used without limitation. In one embodiment of the present invention, it was linked by a short peptide linker between $G_1$-$G_4S$, in which $G_1$ includes the sequence G, and the $G_4S$ includes the sequence GGGGS (SEQ ID NO: 34).

In particular, the cytokine can naturally form a trimer in the cytokine trimer domain of the present invention, but in the case where a fusion protein to which an antibody is bound is prepared by using the trimer structure in its natural state, mismatched disulfide bonds occur in the hinge portion connecting the Fab 3 portion of the antibody to each of the trimers, resulting in a problem of poor purity and productivity. Therefore, in order to increase productivity with higher purity, it is desirable to form a structure of knob-into-hole by at least one amino acid residue of the first or second monomer constituting the dimer and at least one amino acid residue of the third monomer. The knob-into-hole structure is preferably formed in a region other than the cytokine-receptor binding region.

In addition, the at least one amino acid residue is characterized in that it is located on the protein interface. In particular, since the first monomer and the second monomer are connected in tandem through a linker, a hole may be formed in the first monomer or in the second monomer depending on the interface position of the knob generated in the third monomer.

Through the knob-into-hole structure as described above, a selective interaction is induced between one of the first or second monomers constituting the dimer in which the hole is formed and the third monomer in which the knob is formed, and a steric hindrance may be induced at the interface between the remaining first or second monomer in which no holes are formed and the third monomer so as to induce interaction with the desired interface and to inhibit mismatch caused when a natural trimer is used. That is, for example, in the present invention, an interaction may be induced at the interface where the hole of the first monomer and the knob of the third monomer are formed, and a steric hindrance may be induced between the second monomer and the third monomer; or interaction may be induced at the interface where the hole of the second monomer and the knob of the third monomer are formed, and a steric hindrance may be induced between the first monomer and the third monomer.

Meanwhile, in protein-protein interaction, three important interactions [hydrogen bond=2.4-3.2 Å, hydrophobic interaction=3.2-3.9 Å, and charge interaction=~4 Å] typically occur within a distance of 4 Å.

Therefore, in the amino acid residues of the first monomer, the second monomer or the third monomer of the present invention, at least one amino acid residue of the first monomer and amino acid residue of the third monomer may be located at a distance of 6 Å or less, and at least one amino acid residue of the second monomer and at least one amino acid residue of the third monomer may be located at a distance of 6 Å or less, preferably, the at least one amino acid residue of the first monomer and the at least one amino acid residue of the third monomer may be located at a distance of 4 Å or less, and the at least one amino acid residue of the second monomer and the at least one amino acid residue of the third monomer may be located at a distance of 4 Å or less, and more preferably, the at least one amino acid residue of the first monomer and the one amino acid residue of the third monomer may be located at a distance of 2 to 4 Å, and the at least one amino acid residue of the second monomer and the at least one amino acid residue of the third monomer may be located at a distance of 2 to 4 Å.

Therefore, the amino acid residue can be selected from amino acid residues located at a distance of 6 Å or less between the dimer and the monomer, preferably at a distance of 4 Å or less, and more preferably at a distance of 2 to 4 Å, and for example, when the cytokine consists of 4-1BBL monomers and dimers, it may be at least one selected from the group consisting of F92, F238, Q94, F144, V234, Q146, E148, F199, Y142, L203, R202, Q200, and A180.

The position of the amino acid mutation was determined based on the amino acid sequence of TNFSF9 (TNF superfamily member 9) (4-1BB ligand or 4-1BBL) of NCBI (accession number: NM_003811.3) characterized by amino acid sequence represented by SEQ ID NO: 35.

More preferably, amino acid mutation of each monomer may be induced, thereby forming a knob-into-hole structure. Accordingly, the amino acid residue may be at least one selected from the group consisting of F92W, F238V, Q94S, Q94Y, F144I, V234H, V234F, V234R, Q146S, E148G, F199L, Y142T, L203A, R202V, R202W, R202F, F199W, and A180E.

More preferably, the amino acid residue may be one in which two amino acid residues are paired to form a knob-into-hole. Even more preferably, the amino acid residue is characterized in that R202W and Q94S are paired to form a knob-into-hole structure.

For cytokines such as 4-1BBL, E148G of a dimer (first monomer and second monomer are linked by a linker) (hole formation) and A180E of a monomer (third monomer) (knob formation) can prepare a trimer that forms a knob-into-hole. In addition, R202V of a dimer (first monomer and second monomer are linked by a linker) (hole formation) and V234R of a monomer (third monomer) (knob formation) can prepare a trimer that forms a knob-into-hole. Further, Q94S of a dimer (first monomer and second monomer are linked by a linker) (hole formation) and R202W of a monomer (third monomer) (knob formation) can prepare a trimer that forms a knob-into-hole.

According to an embodiment of the present invention, for cytokines such as 4-1BBL, Q94S of a dimer (first monomer and second monomer are linked by a linker) (hole formation) and R202W of a monomer (third monomer) (knob formation) prepared a trimer that forms a knob-into-hole.

Figure 2:
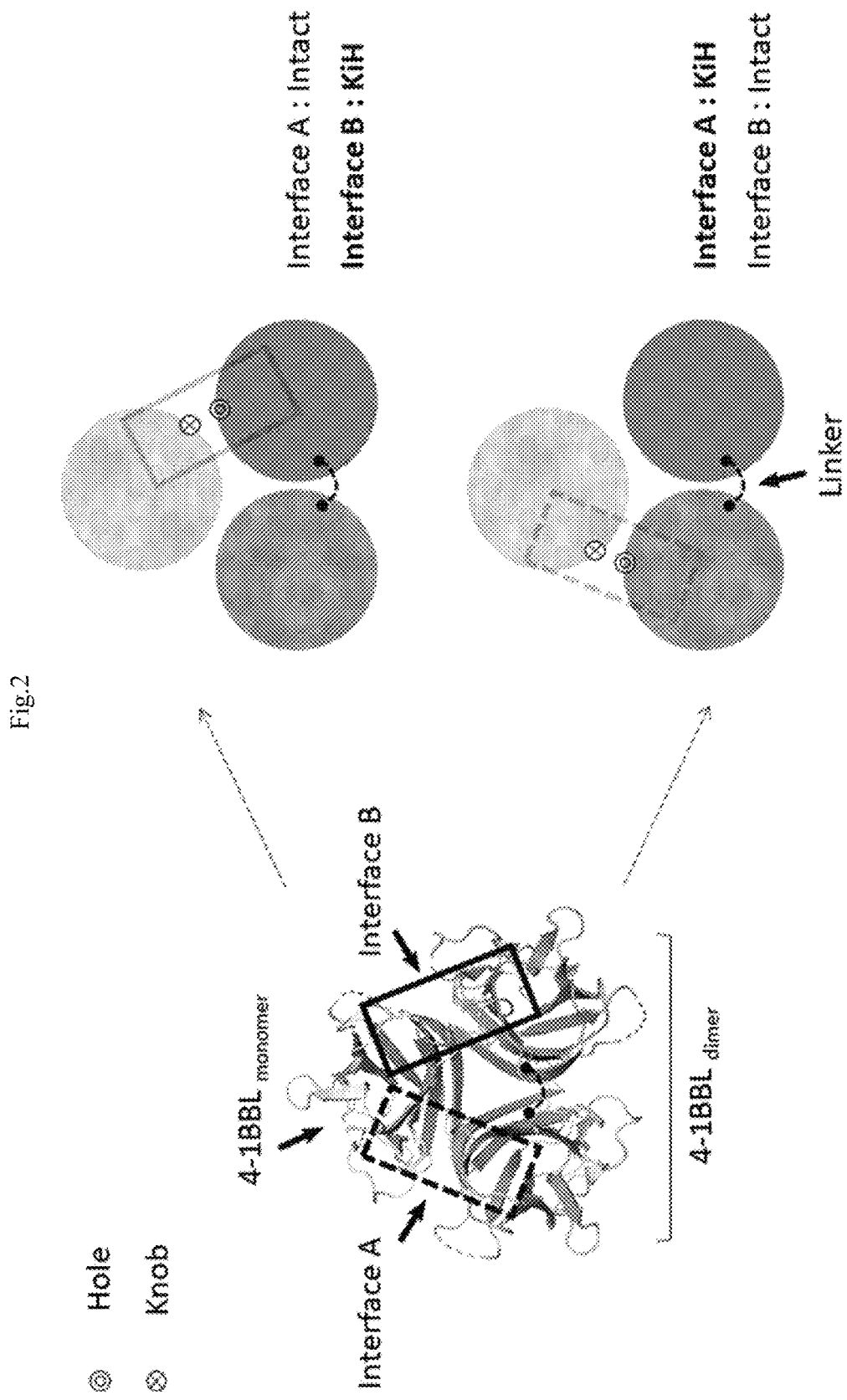
FIG. 2 is a view of explaining the structure of the knob-into-hole in the cytokine trimer domain according to the present invention.

In addition, as shown in FIG. 2, two interfaces are formed between the dimer and the monomer having the knob-into-hole structure as described above (Interface A and Interface B (knob-into-hole (KiH)). Therefore, the present invention is to achieve selective trimerization with minimal changes, and the interface opposite to which Interface B (knob-into-hole (KiH)) is applied can maintain a natural interface. Therefore, the trimer according to the present invention is characterized in that the three monomers maintain a parallel trimer structure.

In the fusion protein of the present invention, the antigen binding domain is an antibody or antibody fragment.

In the fusion protein of the present invention, any antibody or antibody fragment may be used without limitation, as long as the antibody or antibody fragment is capable of binding to the desired antigen. In an embodiment of the present invention, a fusion protein including any one antibody selected from the group consisting of rituximab, cetuximab, trastuzumab, and avelumab and a cytokine trimer domain was prepared.

The antibody fragment may include a light chain variable region and a heavy chain variable region and may preferably include at least one selected from the group consisting of Fab, Fab', F(ab')2, scFv, di-scFv, and VHH (variable heavy chain domains of heavy chain antibody).

In particular, the antibody fragment has an N-terminus or C-terminus linked to a cytokine trimer to form a fusion protein. More preferably, the antibody fragment may be F(ab')2 having the following structure: the first hinge of F(ab')2 is linked to a first monomer or a second monomer linked by a linker; and the second hinge of the F(ab')2' is linked to the third monomer.

In the fusion protein of the present invention, the cytokine is characterized in that it binds to the receptor in the form of a trimer in a natural state.

Therefore, the cytokine may preferably be a tumor necrosis factor superfamily (TNFSF) capable of trimer formation in a natural state. Preferably, it may be at least one selected from the group consisting of TNFα, Dif, Necrosin, TNFβ, TNFSF1B, TNFγ, CD252, Gp34, CD134L, CD154, TRAP, Gp39, T-BAM, CD178, APTL, CD95L, CD70, CD153, and 4-1 BBL and more preferably 4-1 BBL.

According to an embodiment of the present invention, in the fusion protein of the present invention, a globular protein domain exposed to the outside of the cell was used among the entire sequence of 4-1BB (Accession number: NM_003811.3) (G90-T241), and thus the 4-1BBL is characterized in that it includes the amino acid sequence represented by SEQ ID NO: 17.

(SEQ ID NO: 17)
GMFAQLVAQNVLLIDGPLSWYSDPGLAGVSLTGGLSYKEDTKELVVAKA

GVYYVFFQLELRRVVAGEGSGSVSLALHLQPLRSAAGAAALALTVDLPP

-continued
ASSEARNSAFGFQGRLLHLSAGQRLGVHLHTEARARHAWQLTQGATVLG

LFRVT

Even more preferably, the trimer 4-1BBL included in the fusion protein may have the following structure: the first 4-1BBL monomer and the second 4-1BBL monomer are linked by a linker; and at least one amino acid residue of the first 4-1BBL monomer or the second 4-1BBL monomer and at least one amino acid residue of the third 4-1BBL monomer form a knob-into-hole structure.

Figure 1B:
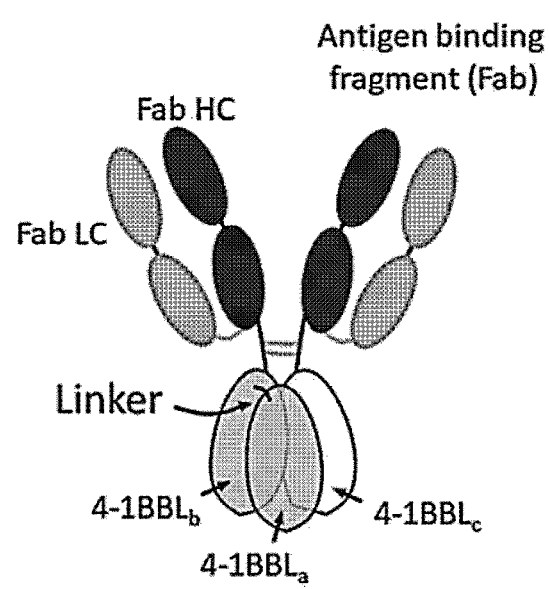

The structure of the 4-1 BBL-based fusion protein prepared according to an embodiment of the present invention is shown in FIGS. 1A and 1B. The fusion protein of the present invention has a structure as shown in FIG. 1B composed of a monomeric protein as shown in FIG. 1A. More specifically, it is composed of three types: 1) an antibody heavy chain including a 4-1BB ligand dimer, 2) an antibody heavy chain including a 4-1BB ligand monomer, and 3) an antibody light chain. In FIG. 1B, the antigen binding fragment at the upper end is connected to the 4-1BB ligand trimer at the lower end through a hinge. The composite is formed through the hydrophobic interaction between the two disulfide bonds at the hinge and the 4-1BB ligand trimer. In particular, the hydrophobic interaction between the ligand trimer is selectively made between the 4-1BB ligand dimer and the 4-1BB ligand monomer through the knob-into-hole module, which can significantly improve the protein properties and purity. The 4-1BBL monomer always has a structure including a knob, which is essential to inhibit homo-trimerization of the heavy chain containing the monomer. The 4-1BB ligand dimer is linked through a short amino acid linker present between the two monomers and has a 'hole' at the site where it interacts with the 'knob' of the opposite monomer.

In a specific embodiment of the cytokine trimer domain of the present invention based on the above, it may include a monomer including the amino acid sequence represented by SEQ ID NO: 1 and a dimer including the amino acid sequence represented by SEQ ID NO: 2. In the dimer, two monomers may be linked by a linker at the 170th amino acid sequence (G). Also, it may include a monomer including the nucleotide sequence represented by SEQ ID NO: 3 and a dimer including the nucleotide sequence represented by SEQ ID NO: 4. In the dimer, two monomers may be linked by a linker in GGA of the 508th to 510th nucleotide sequence.

In another specific embodiment of the cytokine trimer domain of the present invention, it may include a monomer including the amino acid sequence represented by SEQ ID NO: 5 (mutated from R to W in the 202nd amino acid sequence) and a dimer including the amino acid sequence represented by SEQ ID NO: 6 (mutated from Q to S in the 94th amino acid sequence). In the dimer, two monomers may be linked by a linker at the 170th amino acid sequence (G). In addition, the monomer and the dimer may form a knob-into-hole structure at the amino acid mutation position. Also, it may include a monomer including the nucleotide sequence represented by SEQ ID NO: 7 (mutated from AGA to TGG in the 202nd amino acid sequence) and a dimer including the nucleotide sequence represented by SEQ ID NO: 8 (mutated from CAG to AGC in the 94th amino acid sequence). In the dimer, two monomers may be linked by a linker in GGA of the 508th to 510th nucleotide sequence.

In still another specific embodiment of the cytokine trimer domain of the present invention, a monomer including the amino acid sequence represented by SEQ ID NO: 9 (mutated from A to E in the 180th amino acid sequence) and a dimer including the amino acid sequence represented by SEQ ID NO: 10 (mutated from E to G in the 148th amino acid sequence). In the dimer, two monomers may be linked by a linker at the 170th amino acid sequence (G). In addition, the monomer and the dimer may form a knob-into-hole structure at the amino acid mutation position. Also, it may include a monomer including the nucleotide sequence represented by SEQ ID NO: 11 (mutated from GCT to GAA in the 180th amino acid sequence) and a dimer including the nucleotide sequence represented by SEQ ID NO: 12 (mutated from CAA to GGA in the 148th amino acid sequence). In the dimer, two monomers may be linked by a linker in GGA of the 508th to 510th nucleotide sequence.

In yet another specific embodiment of the cytokine trimer domain of the present invention, a monomer including the amino acid sequence represented by SEQ ID NO: 13 (mutated from V to R in the 234th amino acid sequence) and a dimer including the amino acid sequence represented by SEQ ID NO: 14 (mutated from R to V in the 202nd amino acid sequence). In the dimer, two monomers may be linked by a linker at the 170th amino acid sequence (G). In addition, the monomer and the dimer may form a knob-into-hole structure at the amino acid mutation position. Also, it may include a monomer including the nucleotide sequence represented by SEQ ID NO: (mutated from GTG to AGA in the 234th amino acid sequence) and a dimer including the nucleotide sequence represented by SEQ ID NO: 16 (mutated from AGA to GTG in the 202nd amino acid sequence). In the dimer, two monomers may be linked by a linker in GGA of the 508th to 510th nucleotide sequence.

Therefore, the fusion protein of the present invention may preferably include any one cytokine trimer domain selected from the group consisting of a cytokine trimer domain including a monomer including the amino acid sequence represented by SEQ ID NO: 1 and a dimer including the amino acid sequence represented by SEQ ID NO: 2; a cytokine trimer domain including a monomer including the amino acid sequence represented by SEQ ID NO: 5 and a dimer including the amino acid sequence represented by SEQ ID NO: 6; a cytokine trimer domain including a monomer including the amino acid sequence represented by SEQ ID NO: 9 and a dimer including the amino acid sequence represented by SEQ ID NO: 10; and a cytokine trimer domain including a monomer including the amino acid sequence represented by SEQ ID NO: 13 and a dimer including the amino acid sequence represented by SEQ ID NO: 14.

It is clear to those skilled in the art that the amino acid sequences represented by SEQ ID NO: 1, SEQ ID NO: 2, SEQ ID NO: 5, SEQ ID NO: 6, SEQ ID NO: 9, SEQ ID NO: 10, SEQ ID NO: 13, and SEQ ID NO: 14 will be limited to including a mutation of the amino acid sequence exhibiting equivalent biological activity thereof. Such amino acid mutations are made based on the relative similarity such as hydrophobicity, hydrophilicity, charge, size, etc. of amino acid side chain substituents. According to the analysis of the size, shape, and type of amino acid side chain substituents, it can be seen that arginine, lysine, and histidine are all positively charged residues; alanine, glycine, and serine have similar sizes; and phenylalanine, tryptophan, and tyrosine have similar shapes. Therefore, based on these considerations, arginine, lysine, and histidine; alanine, glycine, and serine; and phenylalanine, tryptophan, and tyrosine can be biologically functional equivalents.

For the introduction of mutations, the hydropathic index of amino acids may be considered. Each amino acid is assigned a hydrophobicity index according to its hydrophobicity and charge: isoleucine (+4.5); valine (+4.2); leucine (+3.8); phenylalanine (+2.8); cysteine/cystaine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The hydrophobic amino acid index is very important in imparting the interactive biological function of proteins or peptides. It is well known that substitution with an amino acid having a similar hydrophobic index can retain similar biological activities. When a mutation is introduced with reference to a hydrophobic index, the substitution is made between amino acids showing a hydrophobic index difference preferably within ±2, more preferably within ±1, even more preferably within ±0.5.

Meanwhile, it is also well known that the substitution between amino acids with similar hydrophilicity values leads to proteins or peptides with equivalent biological activity. The following hydrophilicity values are assigned to each amino acid residue: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4).

When a mutation is introduced with reference to a hydrophilicity value, the substitution is made between amino acids showing a hydrophilicity value difference preferably within ±2, more preferably within ±1, and even more preferably within ±0.5.

Amino acid substitution in peptides that do not totally alter the activity of the molecule is known in the art. The substitution occurs the most commonly between amino acid residues, e.g., Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Considering the mutation having the above-mentioned biological equivalent activity, the amino acid sequences represented by SEQ ID NO: 1, SEQ ID NO: 2, SEQ ID NO: 5, SEQ ID NO: 6, SEQ ID NO: 9, SEQ ID NO: 10, SEQ ID NO: 13, and SEQ ID NO: 14 of the present invention are interpreted to include sequences showing substantial identity with the sequence described in sequence lists. The substantial identity means a sequence showing at least 80% homology, more preferably 90% homology by aligning the amino acid sequence represented by SEQ ID NO: 1, SEQ ID NO: 2, SEQ ID NO: 5, SEQ ID NO: 6, SEQ ID NO: 9, SEQ ID NO: 10, SEQ ID NO: 13, and SEQ ID NO: 14 of the present invention with any other sequence as much as possible and analyzing the aligned sequence using algorithms commonly used in the art. The alignment method for sequence comparison may be any method known in the art without limitation.

In addition, the nucleotide sequences represented by SEQ ID NO: 3, SEQ ID NO: 4, SEQ ID NO: 7, SEQ ID NO: 8, SEQ ID NO: 11, SEQ ID NO: 12, SEQ ID NO: 15, and SEQ ID NO: 16 may include a nucleotide sequence having 70% or more, more preferably 80% or more, even more preferably 90% or more, most preferably 95% or more sequence homology with the nucleotide sequences represented by SEQ ID NO: 3, SEQ ID NO: 4, SEQ ID NO: 7, SEQ ID NO: 8, SEQ ID NO: 11, SEQ ID NO: 12, SEQ ID NO: 15, and SEQ ID NO: 16. The "% of sequence homology" for a nucleotide sequence is determined by comparing two optimally aligned sequences with a comparison region, and a portion of the nucleotide sequence in the comparison region may include addition or deletion (i.e., gap) compared to the reference sequence (without addition or deletion) for the optimal alignment of the two sequences.

As mentioned above, in the cytokine trimer domain of the fusion protein according to the present invention, the knob-into-hole structure is characterized in that it is generated through amino acid mutations that occur in monomers and dimers, respectively. This is to inhibit the formation of disulfide mismatched by misassembly of the sequence of the hinge portion connecting the antibody (Fab) in the trimer assembly of the tumor necrosis factor superfamily (TNFSF), which exists as a trimer in nature.

In addition, the present invention provides a polynucleotide encoding the fusion protein according to the present invention.

Further, the present invention provides a vector including a polynucleotide encoding the fusion protein according to the present invention.

Figure 17:
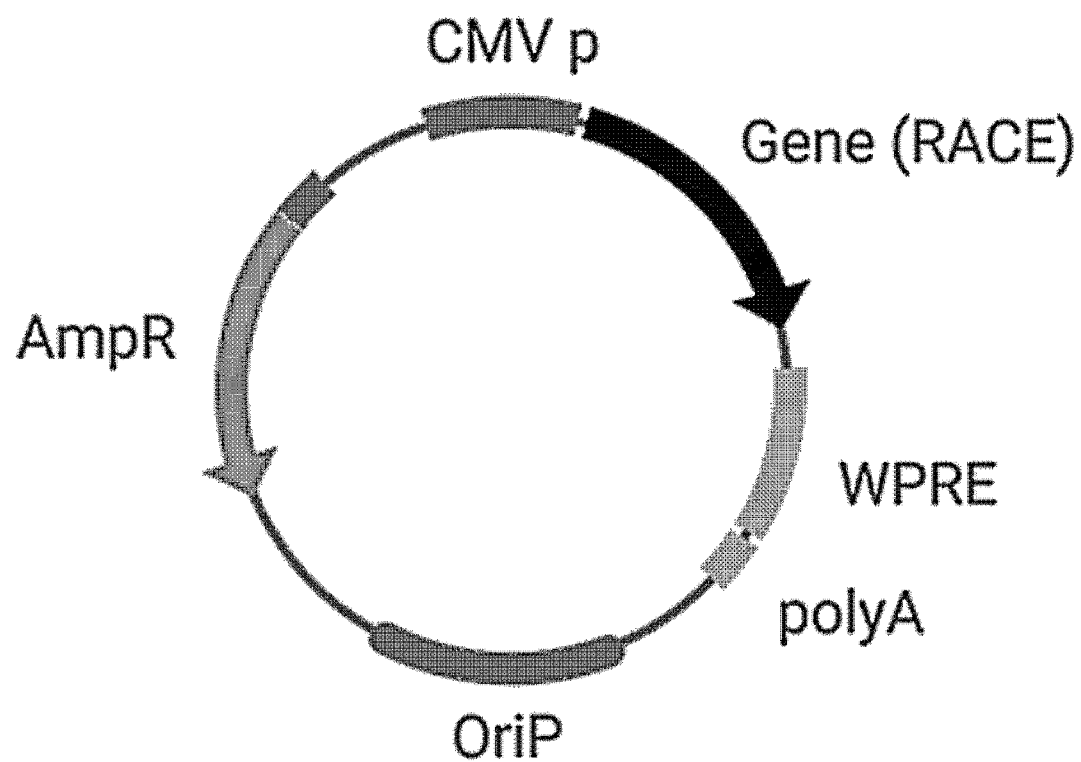
FIG. 17 is a schematic view of a vector including a polynucleotide encoding a fusion protein including an antibody domain and a cytokine trimer according to the present invention.

A schematic diagram of the vector is shown in FIG. 17. In FIG. 17, it is characterized in that the gene region of the vector contains a light chain, a heavy chain dimer, and/or a heavy chain monomer.

In addition, the present invention provides a vector composition for producing a fusion protein including: a first vector in which a polynucleotide encoding the heavy chain of the Fab and a polynucleotide encoding the first monomer and the second monomer connected by a linker are operably linked; a second vector in which a polynucleotide encoding the heavy chain of the Fab and a polynucleotide encoding the third monomer are operably linked; and a third vector including a polynucleotide encoding the light chain of the Fab.

When the vector composition for producing a fusion protein is used, a dimer and a heavy chain of Fab in a trimer and a monomer and a heavy chain of Fab in a trimer, respectively, are prepared, and then the formation of a trimer may be induced.

In the present invention, the "vector" refers to a gene construct including the nucleotide sequence of a gene operably linked to a suitable regulatory sequence so as to express a target gene in a suitable host, and the regulatory sequence may include promoters capable of initiating transcription, any optional operator sequences to control such transcription, and sequences to control the termination of transcription and translation. The vector of the present invention is not particularly limited as long as it can replicate within a cell, and any vector known in the art may be used, for example, a plasmid, cosmid, phage particle, or viral vector.

In addition, the present invention provides a method for producing a fusion protein, the method including a step of infecting a host cell with a vector including a polynucleotide encoding the fusion protein according to the present invention.

In addition, the present invention provides a method for producing a fusion protein, the method including a step of infecting a host cell with the vector composition for producing the fusion protein of claim 1, the composition including: a first vector in which a polynucleotide encoding the heavy chain of the Fab and a polynucleotide encoding the first monomer and the second monomer connected by a linker are operably linked; a second vector in which a polynucleotide encoding the heavy chain of the Fab and a polynucleotide encoding the third monomer are operably linked; and a third vector including a polynucleotide encoding the light chain of the Fab.

In the present invention, the "recombinant vector" may be used as an expression vector of a target polypeptide capable of expressing the target polypeptide with high efficiency in an appropriate host cell when the gene encoding the target polypeptide to be expressed is operably linked, and the recombinant vector can be expressed in a host cell. The host cell may preferably be a eukaryotic cell, and according to the type of host cell, an expression control sequence such as a promoter, terminator, enhancer, etc., and a sequence for membrane targeting or secretion may be appropriately selected and combined in various ways depending on the purpose.

According to an embodiment of the present invention, the fusion protein including an antigen binding domain; and a cytokine trimer domain according to the present invention had superior antigen-binding ability than the parent antibody, and had the superior binding ability to the cytokine target receptor than the parent antibody, and they can bind at the same time. As a result, it was confirmed that each target (protein) could successfully induce binding of the expressed cells.

In addition, the present invention provides a method for producing antibody and tumor necrosis factor superfamily (TNFSF) trimeric fusion protein, in which the tumor necrosis factor superfamily forms a trimer including a dimer including a first and second monomers of the tumor necrosis factor superfamily; and a third monomer of the tumor necrosis factor superfamily, the method including steps: 1) selecting one of the two interfaces present between the dimer and the third monomer; 2) selecting an amino acid pair located at a distance of 6 Å or less between the first or second monomer and the third monomer located at the selected first interface in the first or second monomer; and from the third monomer; 3) forming a knob by inducing a mutation in the third monomer site in the selected amino acid pair; 4) selecting the amino acid residues of the first or second monomers of the wild type (WT) causing a steric hindrance, which are paired with the knob of the third monomer; 5) forming a hole by inducing a mutation in the amino acid residue of the selected first or second monomer; and 6) inducing a knob-into-hole interaction between the knob of the third monomer and the hole of the first or second monomer, in which the heavy chain of the Fab is linked to the dimer and the third monomer.

In step 2) of the method of producing the antibody and tumor necrosis factor superfamily trimeric fusion protein, the amino acid pair may be located at a distance of 6 Å or less, preferably 4 Å or less, and more preferably 2 to 4 Å between the first or second monomer and the third monomer located at the first interface.

In the method of producing the antibody and tumor necrosis factor superfamily trimeric fusion protein, the amino acid residue causing a steric hindrance to the knob may be inferred by changing the corresponding residue to any one amino acid residue selected from the group consisting of glycine (G), valine (V), serine (S), and alanine (A), which is a candidate, through simulation.

In addition, the knob-into-hole coupling is made at the interface selected in step 1), and steric hindrance is induced between the remaining monomers of the unselected interface. Interaction can be induced with the desired interface through the steric hindrance. Therefore, it is possible to inhibit the generation of mismatched disulfide in the hinge portion connecting the antibody (Fab), which may be induced when the fusion protein is produced using the native trimer.

According to an embodiment of the present invention, it was confirmed that in the case of a fusion protein combining an antibody with a cytokine to which the knob-into-hole structure is not applied, unpaired cysteine residues were found near the hinge region where cysteine residues pair to form a disulfide bond, or disulfide bonds in which all three hinges were asymmetrically paired were found.

Therefore, the production method according to the present invention is an optimal method for inhibiting heterogeneity due to abnormal disulfide bonds of the hinge portion in the produced antibody and tumor necrosis factor superfamily trimeric fusion protein to increase the productivity and purity of the fusion protein and is a method that can provide the fusion protein as a more stable therapeutic protein.

The dimer is characterized in that the first monomer and the second monomer are linked by a linker. The dimer is characterized in that the N or C terminus of the first monomer is interconnected with the N or C terminus of the second monomer by a linker. The linker may be used without limitation as long as it is a linker capable of linking the first and second monomers of the cytokine among linkers known in the art.

In addition, any antibody fragment (Fab) may be used without limitation, as long as it can bind to the desired antigen.

In addition, the present invention provides an antibody and tumor necrosis factor superfamily trimeric fusion protein produced by the above production method.

The description of the fusion protein described above is equally applicable to the antibody and tumor necrosis factor superfamily trimeric fusion protein produced by the production method.

Further, the present invention provides a pharmaceutical composition for functional improvement of immune cells to inhibit or treat a disease caused by the functional inactivation or impairment of host immune cells, the composition including the fusion protein according to the present invention.

In addition, the present invention provides a method for treating a disease caused by the functional inactivation or impairment of host immune cells, the method including a step of administering the fusion protein according to the present invention to a subject.

The subject is preferably a mammal, including a human and is a patient in need of treatment for a disease by functional inactivation or impairment of host immune cells, including all patients undergoing treatment for diseases caused by functional inactivation or impairment of host immune cells, patients who have been treated for diseases caused by functional inactivation or impairment of host immune cells, and patients in need of treatment for diseases caused by functional inactivation or impairment of host immune cells and may also include patients who have undergone surgery to treat diseases caused by functional inactivation or impairment of host immune cells.

In addition, the fusion protein of the present invention can be treated in combination with an existing drug or treatment method for treating a disease caused by the inactivation or impairment of the function of host immune cells. When the fusion protein of the present invention is co-treated, it may be treated simultaneously or sequentially with other drugs or methods for the treatment of diseases caused by the functional inactivation or impairment of host immune cells.

The disease caused by the functional inactivation or impairment of host immune cells may be any one or more selected from the group consisting of cancer, immune disease, autoimmune disease, central nervous disease, neurodegenerative disease, autoimmune disease, and inflammatory disease, in which cancer may be any one or more selected from the group consisting of breast cancer, lung cancer, colon cancer and colorectal cancer.

In the present invention, the pharmaceutical composition may be characterized by being in the form of capsules, tablets, granules, injections, ointments, powders, or beverages, and the pharmaceutical composition may be characterized by being targeted to humans. The pharmaceutical composition may be formulated in the form of oral preparations such as powders, granules, capsules, tablets, and aqueous suspensions, preparations for external use, suppositories, and sterile injectable solutions, respectively, according to conventional methods, and used, but is not limited thereto.

The pharmaceutical composition of the present invention may further include a pharmaceutically acceptable carrier. As the pharmaceutically acceptable carrier, a binder, a glidant, a disintegrant, an excipient, a solubilizer, a dispersant, a stabilizer, a suspending agent, a pigment, a fragrance, and the like may be used for oral administration, a buffer, a preserving agent, a pain-relieving agent, a solubilizer, an isotonic agent, a stabilizer, and the like may be used in admixture for injections, and a base, an excipient, a lubricant, a preserving agent, and the like may be used for topical administration. The formulations of the pharmaceutical composition of the present invention may be prepared in various ways by being mixed with the pharmaceutically acceptable carrier as described above. For example, for oral administration, the pharmaceutical composition may be formulated in the form of a tablet, a troche, a capsule, an elixir, a suspension, a syrup, a wafer, or the like. For injections, the pharmaceutical composition may be formulated in the form of unit dosage ampoules or multiple dosage forms.

Meanwhile, as examples of carriers, diluents, or excipients suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a fragrance, an emulsifier, a preservative, and the like may further be included.

The route of administration of the pharmaceutical composition of the present invention includes, but is not limited to, oral, intravenous, intramuscular, intraarterial, intramedullary, intradural, intracardiac, transdermal, subcutaneous, intraperitoneal, intranasal, intestinal, topical, sublingual, or rectal route. The term "parenteral" is meant to include subcutaneous, transdermal, intravenous, intramuscular, intra-articular, intra-synovial, intrasternal, intradural, intralesional, and intra-cranial injection or infusion techniques. The pharmaceutical composition of the present invention may also be formulated as suppositories for intrarectal administration.

The pharmaceutical composition of the present invention may vary depending on a variety of factors, including the activity of a certain active ingredient used, the patient's age, body weight, general health status, sex, diet, time of administration, route of administration, rate of excretion, drug combination, and severity of a certain disease to be inhibited or treated. A dose of the pharmaceutical composition may vary depending on the patient's condition, body weight, severity of disease, drug form, route of administration, and duration, and may be appropriately selected by those skilled in the art. Preferably, taking all of the above factors into consideration, it is possible to administer an amount that can obtain the maximum effect with a minimum amount without side effects, and more preferably, it may be administered repeatedly several times a day at an effective dose of 1 to 10000 μg/body weight kg/day, even more preferably 10 to 1000 mg/body weight kg/day. The above dosage does not limit the scope of the present invention in any way.

The above-described contents of the present invention are equally applied to each other as long as they do not contradict each other, and it is also included in the scope of the present invention that those skilled in the art can implement with appropriate changes.

Hereinafter, the present invention will be described in detail through Examples, but the scope of the present invention is not limited only to the Examples below.

Experimental Example 1. Preparation of Cell Lines

The Freestyle293F cell line (Gibco™, R79007) was suspension cultured using a Freestyle 293F expression medium (Gibco™, 12338018) under a condition of 37° C. and 8% $CO_2$ at 120 RPM. In addition, Raji-B cell line (CCL86™, ATCC), MDA-MB-231 cell line (HTB-26™, ATCC), and SW-480 cell line (10228, KCLB) were cultured using a culture medium in which RPMI1640 (Welgene) was added with 10% (v/v) fetal bovine serum (FBS, Gibco™) and PC-9 cell line (CVCL_B260) and HT-29 cell line (HTB-38™, ATCC) were cultured using a culture medium in which DMEM (Welgene) was added with 10% (v/v) FBS under a condition of 37° C. and 5% $CO_2$.

Example 1. Preparation of Fusion Protein Linking Cytokine Trimer Domain and Antibody Domain 1-1. Gene Preparation For the construction of the fusion protein according to the present invention, the following three types of coding sequences were designed: 1) a light chain of an antibody, 2) a sequence in which a 4-1BB ligand monomer is linked to the C-terminus of the antigen-binding site of an antibody heavy chain, and 3) a sequence in which a 4-1BB ligand dimer is linked to the C-terminus of an antigen-binding site of an antibody heavy chain.

In this regard, a human 4-1BB ligand protein was used, and the corresponding gene (NM_003811.3) was synthesized using Geneart. In the present invention, the globular protein domain (G90-T241) exposed to the outside of the cell was used among the entire sequence of the 4-1BB ligand protein. Cloning and mutagenesis of genes were performed using gateway cloning.

1-2. Construction of Vectors for Producing Fusion Proteins

In order to prepare a fusion protein in which the Fc region of an antibody is replaced with a cytokine trimer (hereinafter, referred to as receptor-antibody conjugated (cell) engager (RACE)), a first vector for Fab heavy chain and a cytokine dimer, a second vector for Fab heavy chain and the cytokine monomer and a third vector for the light chain were constructed.

At this time, in the trimer domain of 4-1BB ligand, which is a cytokine, amino acid residues for mutation formation were simulated and selected using Pymol software and Dynamut server (see worldwide website: biosig.unimelb.edu.au/dynamut/).

A trimer domain was constructed using a partial sequence (G90-T241) of 4-1BB ligand as a unit. Specifically, in order to significantly improve the physical properties and purity of the prepared trimer and to inhibit homo-trimerization of the heavy chain containing the monomer, a trimer was formed using a knob-into-hole structure. To this end, 1) an antibody heavy chain including a 4-1BB ligand dimer and 2) an antibody heavy chain including a 4-1BB ligand monomer were used to form knob-into-hole on only one of the two interfaces present between the dimer and the monomer, and selective trimerization was achieved with minimal changes. A knob was formed in the 4-1BB ligand monomer, and a hole was formed in one of the dimers of the 4-1BB ligand. Each unit of the trimer and its bonding form are shown in FIGS. 1A and 1B, and knob-into-holes that may be formed at the interface of each unit are shown in FIG. 2.

Structural analysis of the trimer domain formed as described above was performed using Pymol software (see worldwide website: pymol.org/2/) based on the structure of the human 4-1BBL protein complex (PDB code: 6A3V, 2X29).

Figure 3:
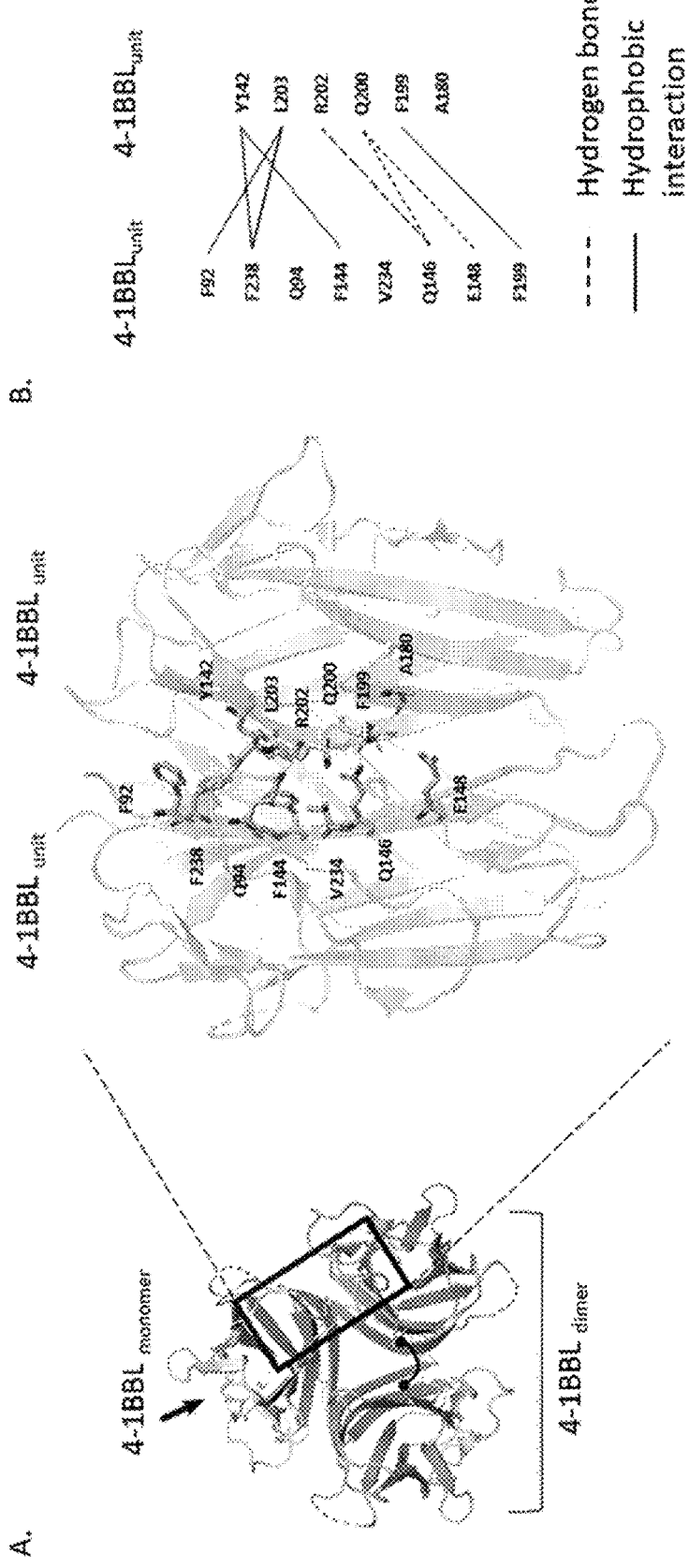
FIGS. 3A and 3B are results of showing the interaction site between the dimer and the monomer, the distance (FIG. 3A), and each interaction (FIG. 3B) in the cytokine trimer domain according to the present invention.

The interaction site between the 4-1BB ligand dimer and the monomer confirmed through this is shown in FIGS. 3A and 3B.

As shown in FIGS. 3A and 3B, amino acids at a distance of less than 4 Å from the interaction interface were identified (FIG. 3A). In addition, the interaction of each amino acid in FIG. 3A is shown as a dotted line (hydrogen bond) or a solid line (hydrophobic interaction) in FIG. 3B.

Figure 4:
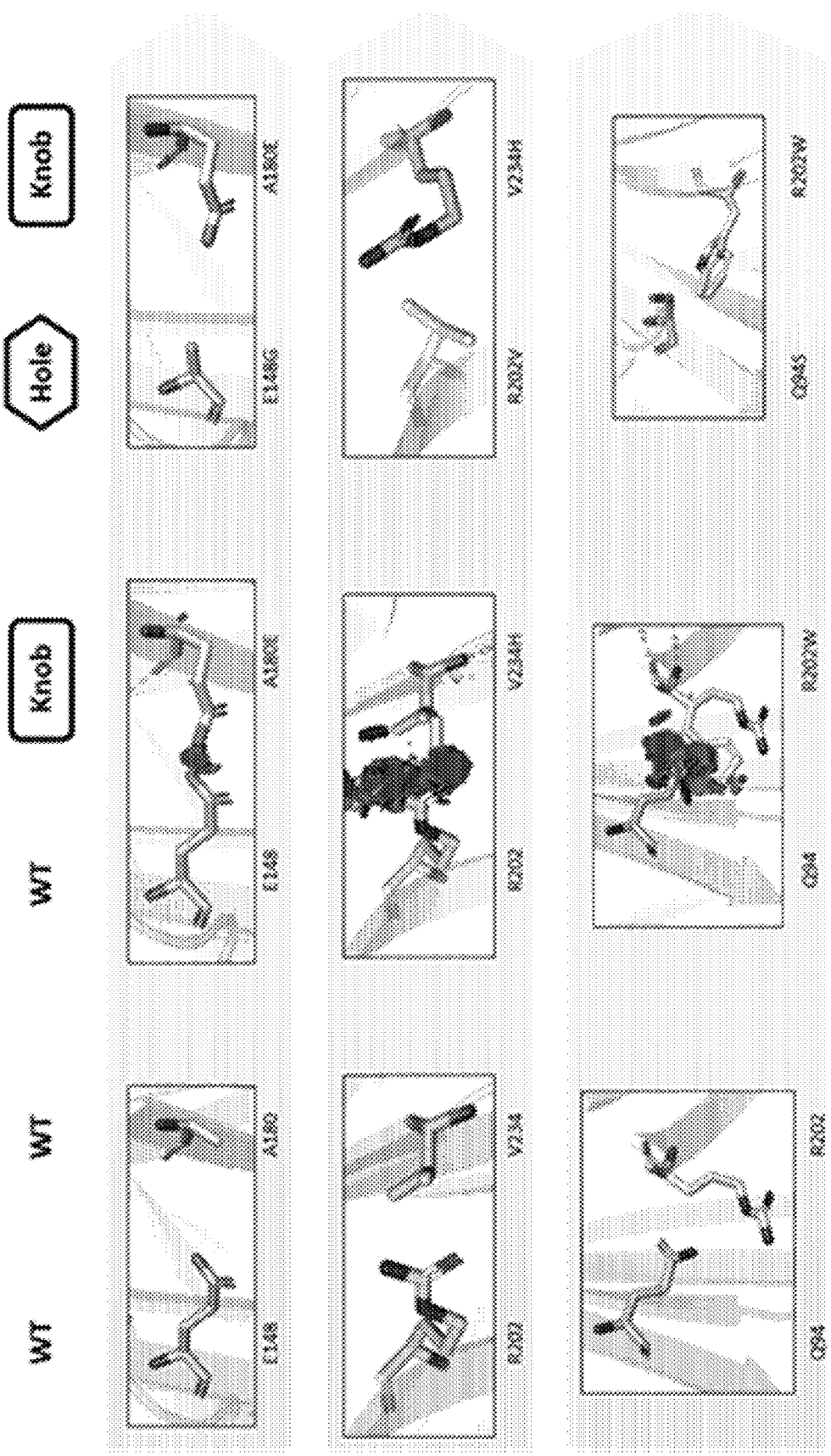
FIG. 4 is a view of comparing the case where the knob is generated only in one direction or the case where the knob and the hole are generated at the same time in the cytokine trimer domain according to the present invention.

The mutation was induced in the amino acid residues derived as described above so as to form a knob-into-hole structure between the dimer and the monomer, and a schematic diagram of whether or not a knob-into-hole was formed in the wild type and each mutation was predicted through mutagenesis and is shown in FIG. 4.

The 4-1BB ligand exists as a trimer in nature. In the assembly of the trimer, misassembly occurs in the sequence of the hinge portion connecting the antibody (Fab) to generate mismatched disulfide. In order to solve this problem, the present invention produced a trimer using a knob-into-hole structure.

As shown in FIG. 4, when no mutation is applied to the amino acid residue of the monomer, the knob-into-hole structure is not formed (left in FIG. 4), and when only the amino acid residue of one monomer is mutated, the mutation occurs at only one side of the interface, and a knob is applied only to the one side of the interface where the mutation has occurred so that interaction with the interface in a natural state may be structurally hindered (steric hindrance) (center in FIG. 4). Therefore, as in the present invention, when both the amino acids of the two monomers are mutated, a knob and a hole are applied to each to form a stable complementary structure (See the right side of FIG. 4).

In consideration of the above, a first vector for the heavy chain-cytokine (dimer) into which the antibody and native cytokine sequences are inserted, a second vector for heavy chain-cytokine (monomer), and a third vector for antibody light chain were prepared. Thereafter, the dimers and monomers were mutagenized to induce the formation of a knob-into-hole structure.

More specifically, for the formation of the knob-into-hole structure, Q94S (hole formation) of the dimer (the first monomer and the second monomer are linked by a linker) and R202W (knob formation) of the monomer (third monomer) were produced to form knob-into-hole.

First, it was commissioned to Geneart (Thermofisher) to synthesize a template (antibody heavy chain, antibody light chain, 4-1BBL(WT) dimer, and monomer) to be used for cloning. At this time, the dimer was synthesized by adding a GGA (Glycine) sequence corresponding to the linker to the 508th to 510th nucleotide sequence. In addition, four types of antibodies were used as the antibody: rituximab (Drugbank accession number (DB00073)), cetuximab (Drugbank accession number (DB00002)), trastuzumab (Drugbank accession number (DB00072)), or avelumab (Drugbank accession number (DB11945)). Thereafter, cloning was performed for each using gateway cloning based on the pCMV vector. More specifically, antibody heavy chain-cytokine dimer in which 4-1BBL-linker-4-1BBL (dimer) is linked to the end of the antibody heavy chain (VH-CH1-hinge) into the multiple cloning site (MCS) of the pCMV vector was inserted to prepare a first vector. To this end, the first fragment for the heavy chain of the antibody, the second fragment for the first monomer among 4-1BBL dimers, and the third fragment for the second monomer among the 4-1BBL dimers were amplified using the primers in Table 1 below, and then gateway cloning was performed.

TABLE 1

| | Direction | Sequence (5'→3') | SEQ ID NO |
|---|---|---|---|
| First Fragment | Forward | tacacgtacttagtcgctgaagctcttcTATGGGATGGAGCTATATC | 18 |
| First Fragment | Reverse | taggtacgaactcgattgacggctcttcATCCCCCCAGGAGTTCAGG | 19 |
| Second Fragment | Forward | tacacgtacttagtcgctgaagctcttcAGGAGGCATGTTTGCCCAGC | 20 |
| Second Fragment | Reverse | TaggtacgaactcgattgacggctcttcAGCCTCCTGTCACTCTGAACAGGCC | 21 |
| Third Fragment | Forward | tacacgtacttagtcgctgaagctcttcAGGCATGTTTGCCCAGC | 22 |
| Third Fragment | Reverse | aggtacgaactcgattgacggctcttcAGAGTTATGTCACTCTGAACAGGCC | 23 |

In addition, the second vector was prepared by inserting the antibody heavy chain-cytokine monomer linking 4-1BBL to the end of the antibody heavy chain (VH-CH1-hinge) into the MCS of the pCMV vector. To this end, the first fragment for the heavy chain of the antibody and the second fragment for the 4-1BBL monomer were amplified using the primers in Table 2 below, and then gateway cloning was performed.

TABLE 2

| | Direction | Sequence (5'→3') | SEQ ID NO |
|---|---|---|---|
| First Fragment | Forward | tacacgtacttagtcgctgaagctcttcTATGGGATGGAGCTATATC | 24 |
| First Fragment | Reverse | taggtacgaactcgattgacggctcttATCCCCCCAGGAGTTCAGG | 25 |
| Second Fragment | Forward | tacacgtacttagtcgctgaagctcttcAGGAGGCATGTTTGCCCAGC | 26 |
| Second Fragment | Reverse | aggtacgaactcgattgacggctcttcAGAGTTATGTCACTCTGAACAGGCC | 27 |

In addition, a third vector was prepared by inserting the antibody light chain into the MCS of the pCMV vector. At this time, the fragment was amplified using the primers in Table 3 below, and then gateway cloning was performed.

TABLE 3

|  | Direction | Sequence (5'→3') | SEQ ID NO |
|---|---|---|---|
| Single Fragment | Forward | TACACGTACTTAGTCGCTGAAGCTCTTCTAG ATCTGTGGCTGCACCA | 28 |
| Single Fragment | Reverse | AGGTACGAACTCGATTGACGGCTCTTCATCT CTTCACTTCCACCTT | 29 |

Thereafter, gateway cloning was performed to apply mutations to the dimer of the first vector and the monomer of the second vector. In this case, the primers in Table 4 below were used. As a result, the mutation of Q94S was applied to the dimer of the first vector, and the mutation of R202W was applied to the monomer of the second vector.

TABLE 4

|  | Direction | Sequence (5'→3') | SEQ ID NO |
|---|---|---|---|
| Dimer (Q94S) | Forward | tacacgtacttagtcgctgaagctcttcTagcCTGGTGGCCCA GAATG | 30 |
| Dimer (Q94S) | Reverse | taggtacgaactcgattgacggctcttcAgctGGCAAACATGC CTCC | 31 |
| Monomer (R202W) | Forward | tacacgtacttagtcgctgaagctcttcTtggCTGCTGCACCTG TCTG | 32 |
| Monomer (R202W) | Reverse | gtacgaactcgattgacggctcttcAccaGCCTTGGAAGCC AAAGGC | 33 |

Whether each gene was inserted or not and sequence verification was confirmed through gene sequencing (requested by Cosmogenetech).

1-3. Transfection and Production of RACE Using First Vector, Second Vector, and Third Vector For transfection and expression of RACE, Freestyle293F cells prepared in Experimental Example 1 were used. The Freestyle293F cell line was prepared at a concentration of $1 \times 10^6$/ml, 24 hours before transfection. The cells were transfected using Fectopro (Polyplus, 116-010) reagent and the first, second, and third vectors prepared above. More specifically, 1 μg of DNA (the first vector, the second vector, and the third vector were mixed in a volume ratio of 1:1:2) and 1 μl of Fectopro reagent were added per 1 ml of the cell line. After additionally suspension culture of the transiently transfected cells for 5 days (37° C., 8% $CO_2$, 120 RPM), the supernatant containing the secreted protein was separated by centrifugation at 1500 g for 30 minutes. The separated supernatant was refrigerated for up to 3 days for subsequent purification.

Example 2. Purification and Purity Analysis of RACE

RACE was purified from the supernatant obtained in Examples 1-3 using AKTA go (Cytiva) and affinity chromatography. Affinity chromatography was performed using a CH1-xL column (Thermo). The washing solution (PBS, pH 7.4) and the elution solution (100 mM sodium acetate pH 4.0) used for chromatography were prepared immediately before use, filtered, and used after measuring the pH. Among the fractions obtained by eluting, the fraction containing the protein was collected together, and it was dialyzed through an Amicon® Ultra (30 kda, 15 ml) filter using a PBS solution and stored.

For purity analysis of purified RACE, size exclusion chromatography (PL1580-3250, Agilent) was performed using high-performance liquid chromatography (HPLC, Agilent 1260). The approximate protein size prediction through size exclusion chromatography was determined by testing using a standard protein (5190-2242, Agilent) having known size. A buffer solution of 150 mM sodium phosphate pH 7.0 was used for purity analysis.

As a result, as shown in FIG. 5, the purity of avelumab-41BBL (RACE-04L) according to the present invention was 97.24% (See the PD-L1 targeting (4AL) graph in FIG. 5), the purity of cetuximab-41BBL (RACE-02B) was 96.47% (See EGFR targeting (Cetuximab) graph in FIG. 5), and the purity of trastuzumab-41BBL (RACE-02C) was 96.91% (See HER2 targeting (Herceptin) graph in FIG. 5), All RACE prepared according to the present invention showed excellent productivity and purity.

In addition, when knob-into-hole (Q94S/R202W) was applied in rituximab-41BBL (RACE-01C) according to the present invention, as shown in FIG. 6A, it was confirmed that the 4-1BB ligand dimer (hole) and 4-1BB ligand monomer (knob) successfully constituted a 4-1BB ligand trimer, and this trimer was composed of a heavy chain-dimer including a hole (Q94S), a heavy chain-monomer including a knob (R202W), and a light chain. In addition, the purification and purity analysis of rituximab-41BBL (RACE-01C) according to the present invention was performed in the same manner as above, and as a result, it was confirmed that it showed a similar level of production to that of a normal antibody having an Fc dimer (FIG. 6B) and the protein was separated into a protein with a high purity of 96% or more after the primary purification based on CH1 (FIG. 6C).

Example 3. Structural Analysis of RACE

The structure of the 4-1BBL trimer domain was analyzed using Pymol software (see worldwide website: pymol.org/2/) based on the structure of the human 4-1BBL protein complex (PDB code: 6A3V, 2X29).

Figure 7:
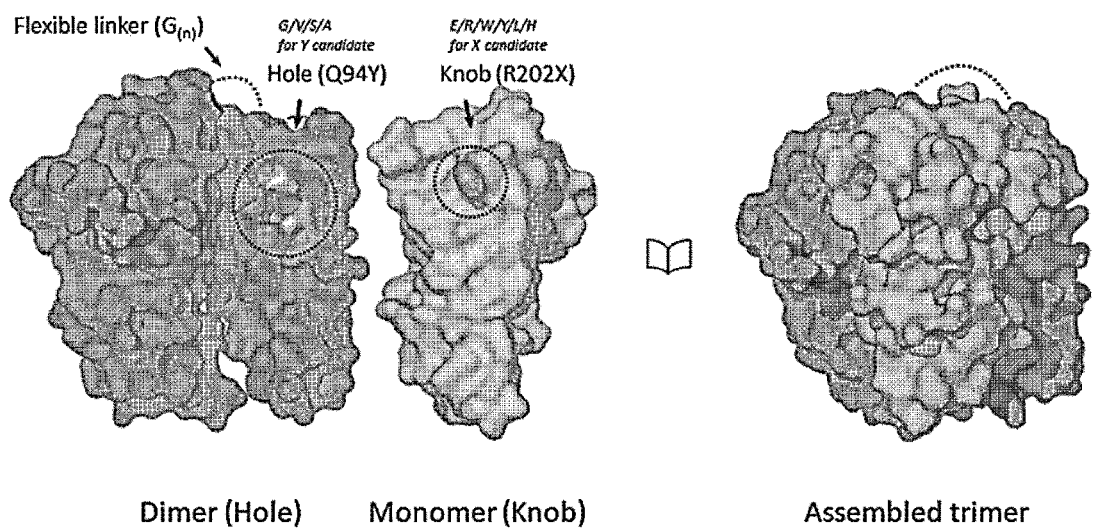
FIG. 7 is a result of confirming the structure of the cytokine trimer domain according to the present invention, confirming that the dimer and the monomer form a knob-into-hole structure.
Figure 8:
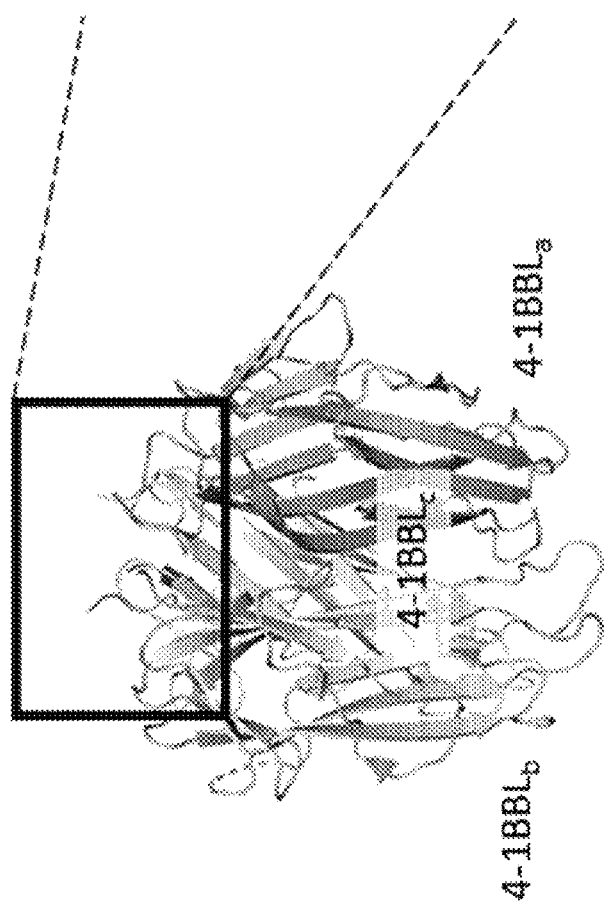
FIG. 8 is a view of showing the structure of the cytokine trimer domain and a linker connecting the dimers according to the present invention.

As a result, as shown in FIGS. 7 and 8, it was confirmed that the C-terminus of 4-1BBL$_a$ constituting the dimer is connected with the N-terminus of 4-1BBL$_b$ by a short peptide linker between $G_1$-$G_4$S, and thus it contributes to the stable expression of the heavy chain including the 4-1BB ligand dimer. In addition, it was confirmed that a hole was formed in the dimer and a knob was formed in the monomer to constitute a trimer.

Example 4. Confirmation of Effect of Mismatch on Trimer Formation

In the 4-1BB ligand bound to RACE according to the present invention, the effect of the knob-into-hole structure application on the protein hinge was confirmed by disulfide bond analysis through LC (Vanquish, Thermo) and MS (Q Exactive Plus, Thermo). For protein fragment formation, analysis samples and standard samples at a concentration of 1 mg/ml, for example, endoproteinase Lys-C(Sigma, USA), and chymotrypsin (Promega), Glu-C (Promega, Sequencing Grade) were used.

The analysis sample was prepared as follows. For the second vector (antibody heavy chain-monomer) and third vector (antibody light chain) of Examples 1-2, rituximab was used as the antibody, and the native type 4-1BBL as the monomer to prepare the recombinant vector. After the prepared recombinant vector was simultaneously transfected into Freestyle293F cells in the same manner as in Example 1-3 above, the supernatant of the cells overexpressing the protein was obtained. The analysis sample was a protein made from RACE heavy chain monomer and a light chain having a native 4-1BBL sequence and had a structure of a RACE trimer having a total of three antibody-binding fragments (Fab) and a hinge region. At this time, the pattern of abnormal disulfide bonds in the protein hinge was observed to confirm the effect of dimerization of the hinge through the knob-into-hole structure on structural stability and homogeneity.

In addition, to confirm the characteristics of the protein multimerized by disulfide bonds, electrophoresis (Mini-protein tetra, Bio-Rad) was performed using SDS-PAGE (Sodium dodecyl sulphate polyacrylamide gel). At this time, the size of each protein was compared under reducing and non-reducing conditions. After the electrophoresis was completed, the gel was stained with Coomassie-blue reagent, and the results were analyzed using LAS-500 (Cytiva).

Figures 9A, 9B:
FIGS. 9A and 9B are results of confirming the protein having a mismatched disulfide bond of the protein hinge (FIG. 9A) and mismatched hinge type and incidence rate (FIG. 9B) when the knob-into-hole structure is not formed in the cytokine trimer domain according to the present invention.

As shown in FIGS. 9A and 9B, in the natural 4-1BB ligand to which the knob-into-hole was not applied, the 4-1BB ligand dimer is referred to as A, and the 4-1BB ligand monomer is referred to as B, and the light chain is referred to as L. In the cell line that overexpressed the natural monomers B and L, to which no knob was applied, misassembled substances such as B3L3 and B2L2 were observed (SDS-PAGE result at the bottom of FIG. 9A). In particular, in the case of B3L3, which has three hinges, an unpaired cysteine residue was found near the hinge region where two cysteine residues pair to form a disulfide bond, or asymmetrically paired disulfide bonds were found in all three hinges (See FIG. 9B). This phenomenon was prominent in the experimental group (YK) treated with chymotrypsin and Lys-C at the same time, and was insignificant in the experimental group (EK) treated with Glu-C and Lys-C at the same time. This heterogeneity is a characteristic that should never be present in therapeutic proteins, and it was clearly confirmed that monomer improvement (given a knob) is absolutely necessary in order to increase the purity and productivity of the final trimer.

Example 5. Fusion Protein (RACE) Prepared by Linking Antibody Domain and Cytokine Trimer and Characteristic Analysis Thereof 5-1. Size Analysis Various types of antigen-binding fragments can be bound to the fusion protein (RACE) platform prepared in Example 1 depending on the purpose, and a structural schematic diagram of RACE bound to an antibody domain is shown in FIG. 10.

In addition, the domain structure of RACE is shown in FIG. 10 by arranging it from the N-terminus to the C-terminus. In the fusion protein according to the present invention, the hinge-connected monomer of the 4-1BB ligand has a knob module, and the dimer of the 4-1BB ligand has a hole module.

5-2. Thermal Shift Assay (TSA)

Measurement of stability and melting temperature (Tm) of RACE was performed with reference to standard test methods using SYPRO™ Orange (S6650, Thermo) reagent.

The thermodynamic stabilities of rituximab-41BBL (RACE-01C) and its parent antibody, rituximab, were compared, and the thermodynamic stabilities of trastuzumab-41BBL (RACE-02C) and its parent antibody, trastuzumab, were compared, and the results are shown in FIG. 11. As a result, it was confirmed that both rituximab-41BBL (RACE-01C) and trastuzumab-41BBL (RACE-02C) according to the present invention had a Tm value of 65° C. or higher and simulated the characteristics of the parent antibody.

5-3. Binding Affinity Measurement

The binding of cetuximab-41BBL (RACE-02B) to antigen (EGFR) according to the present invention was confirmed using Biacore (Cytiva) using surface plasmon resonance (SPR). First, for the measurement of binding force, antigen EGFR (10001-H08H, Sino) or 4-1BB (10041-H08H, Sino) was immobilized on the surface of the sensor chip CM5 chip (29149604, Cytiva) through amine coupling. Afterward, a predetermined concentration of cetuximab-41BBL (RACE-02B) was added thereto. HEPES-buffered saline (HBS) buffer was used to confirm binding for 180 seconds and dissociation for 300 seconds.

Figure 12:
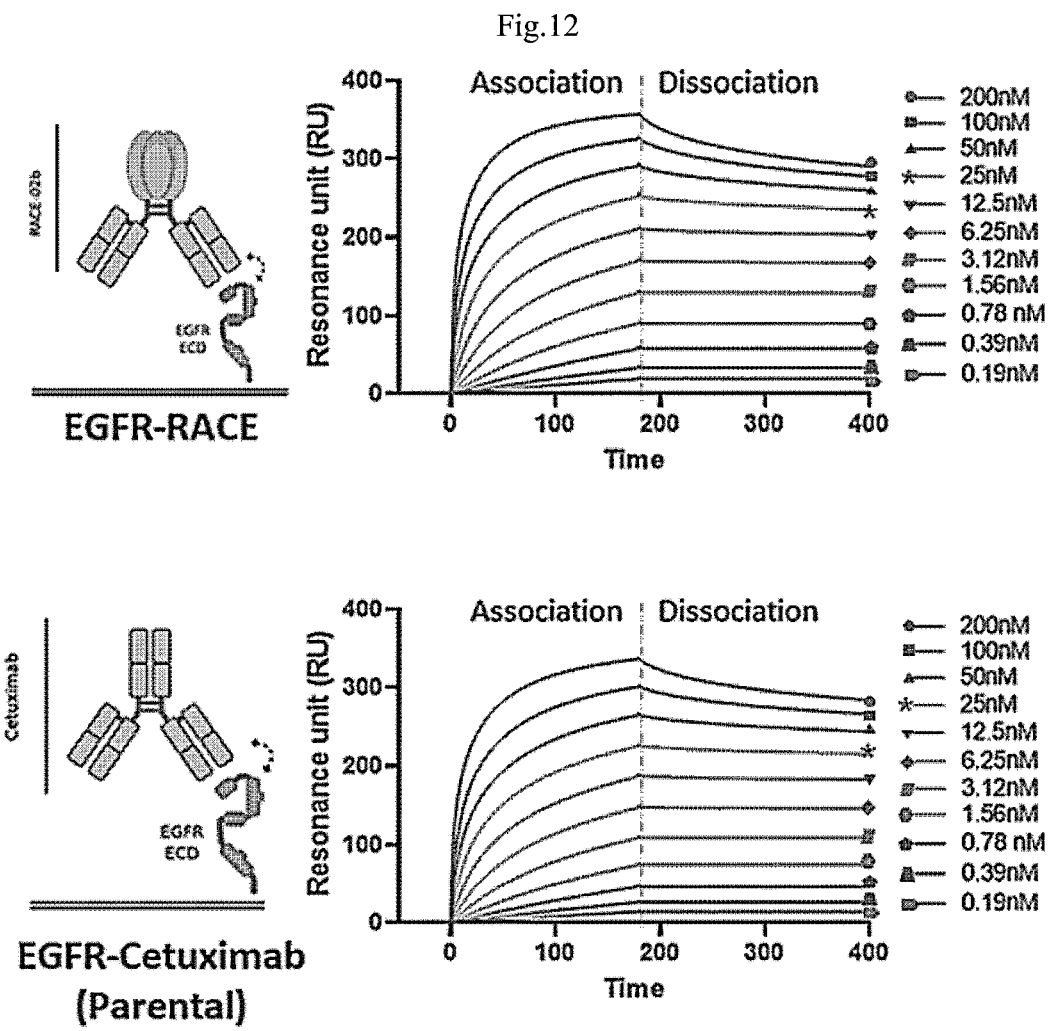
FIG. 12 is a result of confirming the antigen-binding affinity of a fusion protein including an antibody domain and a cytokine trimer according to the present invention.

As a result, as shown in FIG. 12, it was confirmed that cetuximab-41BBL (RACE-02B) according to the present invention showed similar binding ability to the parent antibody, cetuximab.

In addition, as shown in FIG. 13, cetuximab-41BBL (RACE-02B) according to the present invention had a total of three binding sites, one each between each monomer, showing a stable bonding pattern for the 4-1BB receptor (See an upper portion of FIG. 13), and it showed a much stronger binding ability compared to Utomilumab (Pfizer, (4-1BB ligand competitive binding)), which is an aggregating antibody to the 4-1BB receptor.

5-4. Confirmation of Simultaneous Binding Ability of RACE

Figure 14:
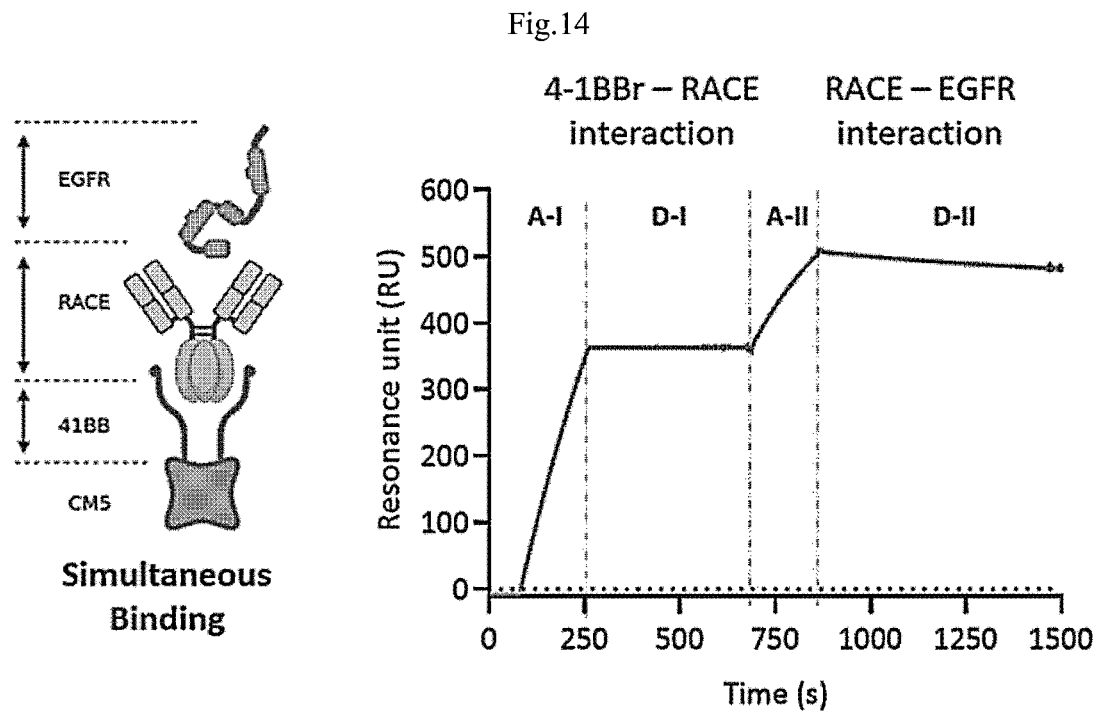
FIG. 14 is a result of confirming the simultaneous binding ability of a fusion protein including an antibody domain and a cytokine trimer according to the present invention for an antigen and a target receptor.

In addition, the simultaneous binding ability of cetuximab-41BBL (RACE-02B) target according to the present invention was confirmed. As shown in the schematic diagram on the left of FIG. 14, after fixing the 4-1BB receptor on the surface of the CM5 chip, binding to cetuximab-41BBL (RACE-02B) was observed (A-I and D-I), and in that state, additional EGFR binding was sequentially observed (A-II and D-II).

As a result, it was confirmed that cetuximab-41BBL (RACE-02B) according to the present invention can bind to both targets at the same time, indicating that binding of each protein-expressed cell can be successfully induced.

5-5. 4-1BB Reporter Assay

The degree of 4-1BB signaling by rituximab-41BBL (RACE-01C) according to the present invention was evaluated using the 4-1BB bioassay (J2332, Promega). The evaluation was performed according to the manufacturer's instructions, and in order to confirm the signal dependence on the target antigen, the CD20-expressing Raji B cell line of Experimental Example 1 was used. The relative value of the signal was measured with a GloMax® Discover Microplate Reader (GM30000, promega) using a GloMax® (Promega).

As a result, as shown in FIG. 15, it was confirmed that rituximab-41BBL (RACE-01C) according to the present invention amplifies the NF-KB reporter signal in a concentration-dependent manner (See the right side of FIG. 15).

Example 6. Confirmation of RACE Signaling Mediated Process in Solid Cancer Cells The signaling mediated process of the fusion protein according to the present invention in solid cancer cells was confirmed. For this purpose, as described in Experimental Example 1, the MDA-MB-231 cell line (breast cancer cell line) known to express very slightly Her2, and the PC-9 cell line (lung adenocarcinoma cell line), the HT-29 cell line (colon cancer cell line), and the SW480 cell line (colorectal cancer cell line) known to overexpress EGFR were treated with trastuzumab-41BBL (RACE-02C), cetuximab-41BBL (RACE-02B) or rituximab-41BBL (RACE-01C) according to the present invention in the same manner as in Example 5-5, and the degree of each 4-1BB signaling was evaluated.

The degree of on-target signaling and off-target signaling for the MDA-MB-231 cell line is shown in FIG. 16A. In the case of the MDA-MB-231 cell line, although it expresses very insignificantly the target protein HER2 enough to be classified as triple-negative breast cancer, when treated with trastuzumab-41BBL (RACE-02C), which can bind to the corresponding protein, it was observed that the degree of signaling sensitively increased according to the concentration, whereas when treating with rituximab-41BBL (RACE-01C), which targets CD20, an antigen that is not expressed at all in the corresponding cells, signal increase according to the concentration was not observed in the off-target. In addition, the degree of EGFR expression and differences in on-target signaling and off-target signaling degrees in three types of tumor cell lines in which EGFR protein was expressed on the surface were shown in FIG. 16B. In FIG. 16B, those marked with cell line-on (e.g., SW480-on, HT-29-on, and PC9-on) show the result of confirming an on-target effect, that is, the degree of signaling after treatment with cetuximab-41BBL (RACE-02B) produced using cetuximab capable of binding to EGFR expressed in each target cell. On the other hand, those marked with -off in the same cell line (e.g., SW480-off, HT-29-off, and PC9-off) show the result of confirming the off-target effect of the drug, that is, the degree of signaling after treatment with rituximab-41BBL (RACE-01C) capable of binding to CD20 that is not expressed at all by each target cell.

As a result, it was possible to confirm signaling in proportion to the concentration upon treatment with cetuximab-41BBL (RACE-02B) for three types of cells overexpressing EGFR, but no signaling could be confirmed upon treatment with rituximab-41BBL (RACE-01C)-target-off for the CD20 protein, which is not expressed at all in each cell line. These results confirmed that there is no off-target toxicity, which has traditionally been a problem with 4-1BBL-targeted therapeutics.

In addition, it was confirmed that the fusion protein cetuximab-41BBL (RACE-02B) according to the present invention is specific to the target antigen and induces 4-1BB signaling to a much superior degree than Utomilumab, a 4-1BB aggregation antibody (FIG. 16B).

Example 7. Confirmation of Efficacy in Cancer-Induced Animal Models

The anticancer efficacy of cetuximab-41BBL (RACE-02B) was confirmed in a cancer-induced animal model. First, it was prepared to express human EGFR on the surface of mouse colorectal cancer cells (CT26) that grow spontaneously in Balb-c mice, and the hEGFR-CT26 cells ($5 \times 10^5$/100 µL) were subcutaneously transplanted into humanized mice (Balb-c) expressing the extracellular domain of human 4-1BB (commissioned for Gempharmatech). Antibodies from the following group were administered via a caudal vein in Q3D (once every 3 days), a total of 6 times, starting from when the transplanted tumor size reached 100 mm³ on average: control (5 mg/kg, human IgG (purchased from Sigma (14506)) and cetuximab-41BBL (RACE-02B) (0.5 mg/kg and 2 mg/kg). The size of the tumor in each experimental group (TV=0.5 a×b²) was measured twice a week with a caliper. In the above, a is the long axis of the tumor, and b is the short axis of the tumor.

Figure 18:
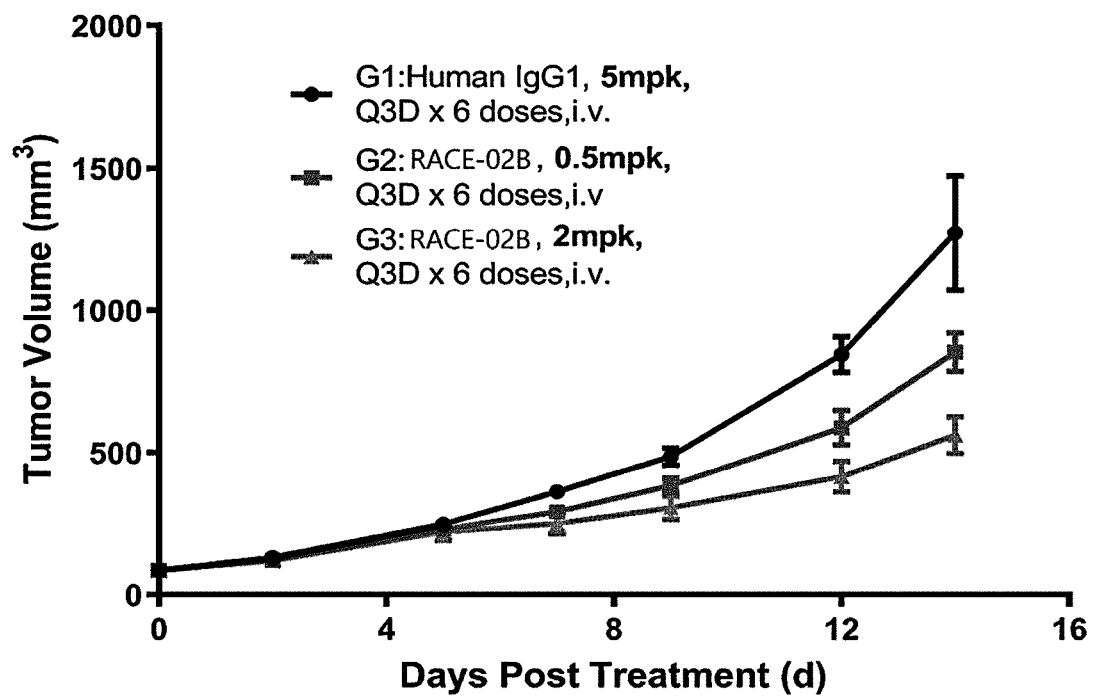
FIG. 18 is a result of confirming the therapeutic effect of a fusion protein including an antibody domain and a cytokine trimer according to the present invention in a tumor-inducing animal model.

As a result, as shown in FIG. 18, cetuximab-41BBL (ARCE-02B) showed significant tumor suppression ability compared to the control, human IgG antibody.

Overall, the present invention relates to a cytokine trimer domain in which a dimer in which a first monomer and a second monomer are linked by a linker and a third monomer are coupled by a knob-into-hole and a novel type of fusion protein (RACE) in which an antibody and a cytokine trimer domain are connected, which is produced by replacing a constant region (Fc) of an antibody with the cytokine trimer domain. Thus, it was confirmed that the cytokine trimer domain bound with the knob-into-hole according to the present invention showed much stronger binding ability than the aggregation antibody to the 4-1BB receptor, and the fusion protein containing the same showed the excellent binding ability to both targets, thereby confirming that each target (protein) can successfully induce the binding of the expressed cells.

The invention claimed is:

1. A fusion protein comprising a cytokine trimer domain having a dimer comprising a first monomer and a second monomer; a third monomer; and an antigen binding domain, wherein the cytokine trimer domain has a knob-into-hole structure formed by at least one amino acid residue of the first monomer or the second monomer and at least one amino acid residue of the third monomer, wherein the cytokine of the cytokine trimer domain is a tumor necrosis factor superfamily (TNFSF) cytokine.

2. The fusion protein of claim 1, wherein the hole structure of the knob-into-hole structure is formed in the dimer comprising the first monomer and the second monomer, and a knob structure of the knob-into-hole structure is formed in the third monomer.

3. The fusion protein of claim 1, wherein the knob-into-hole structure is formed in a region other than a cytokine-receptor binding region.

4. The fusion protein of claim 1, wherein the at least one amino acid residue of the first monomer and the at least one amino acid residue of the third monomer are located at a protein surface; or
wherein the at least one amino acid residue of the second monomer and the at least one amino acid residue of the third monomer are located at a protein surface.

5. The fusion protein of claim 1, wherein the at least one amino acid residue of the first monomer and the at least one amino acid residue of the third monomer are located at a distance of 6 Å or less.

6. The fusion protein of claim 1, wherein the at least one amino acid residue of the second monomer and the at least one amino acid residue of the third monomer are located at a distance of 6 Å or less.

7. The fusion protein of claim 1, wherein the antigen binding domain is an antibody or an antibody fragment.

8. The fusion protein of claim 7, wherein the antibody fragment comprises a light chain variable region and a heavy chain variable region.

9. The fusion protein of claim 7, wherein the antibody fragment comprises at least one selected from the group consisting of Fab, Fab', F(ab')2, scFv, di-scFv, and variable heavy chain domains of heavy chain antibody (VHH).

10. The fusion protein of claim 7, wherein an N-terminus or C-terminus of the antibody fragment is linked to the cytokine trimer domain.

11. The fusion protein of claim 7, wherein the antibody fragment is F(ab')2 having the following structure:
a first hinge of the F(ab')2 is linked to the first monomer or the second monomer; and
a second hinge of the F(ab')2 is linked to the third monomer.

12. The fusion protein of claim 1, wherein the cytokine binds to a receptor in the form of a trimer in a natural state.

13. The fusion protein of claim 1, wherein the tumor necrosis factor superfamily cytokine is at least one selected from the group consisting of TNFα, Dif, Necrosin, TNFβ, TNFSF1B, TNFγ, CD252, Gp34, CD134L, CD154, TRAP, Gp39, T-BAM, CD178, APTL, CD95L, CD70, CD153, and 4-1BBL.

14. The fusion protein of claim 1, wherein the tumor necrosis factor superfamily cytokine is 1BBL.

15. The fusion protein of claim 14, wherein the 4-1BBL comprises the amino acid sequence represented by SEQ ID NO: 17.

16. The fusion protein of claim 14, wherein the 4-1BBL has the following structure:
a first 4-1BBL monomer and a second 4-1BBL monomer linked by a linker; and at least one amino acid residue of the first 4-1BBL monomer or the second 4-1BBL monomer and at least one amino acid residue of a third 4-1BBL monomer form a knob-into-hole structure.

17. The fusion protein of claim 14, wherein the at least one amino acid residue of the first monomer, the second monomer, or the third monomer comprises at least one selected from the group consisting of F92, F238, Q94, F144, V234, Q146, E148, F199, Y142, L203, R202, Q200, and A180 of the amino acid sequence represented by SEQ ID NO: 35,
wherein the 4-1BBL comprises the globular protein domain G90-T241 of the 4-1BBL represented by SEQ ID NO: 35.

18. The fusion protein of claim 17, wherein the at least one amino acid residue of the first monomer, the second monomer, or the third monomer comprises at least one selected from the group consisting of F92W, F238V, Q94S, Q94Y, F144I, V234H, V234F, V234R, Q146S, E148G, F199L, Y142T, L203A, R202V, R202W, R202F, F199W, and A180E.

19. The fusion protein of claim 14, wherein the knob-into-hole structure is formed by at least one pair selected from the group consisting of a pair consisting of A180E and E148G, a pair consisting of V234R and R202V, and a pair of R202W and Q94S.

20. A method for producing an antibody and tumor necrosis factor superfamily (TNFSF) cytokine trimeric fusion protein, wherein the tumor necrosis factor superfamily cytokine forms a trimer comprising a dimer having first and second monomers of the tumor necrosis factor superfamily; cytokine, and the trimer comprising a third monomer of the tumor necrosis factor superfamily cytokine, the method comprising:

a) selecting one of two interfaces present between the dimer and the third monomer;

b) selecting an amino acid pair located at a distance of 6 Å or less between the first or second monomer and the third monomer located at the selected one interface in the first or second monomer; and from the third monomer;

c) forming a knob by inducing a mutation in the third monomer in the selected amino acid pair to form a knob;

d) selecting the amino acid residues of the first or second monomers of a wild type (WT) of tumor necrosis factor superfamily cytokine causing a steric hindrance, which are paired with the knob of the third monomer;

e) forming a hole by inducing a mutation in the amino acid residue of the selected first or second monomer; and f) inducing a knob-into-hole interaction between the knob of the third monomer and the hole of the first or second monomer, wherein a heavy chain of an antibody Fab is linked to the dimer and the third monomer.

21. The method of claim 20, wherein a knob-into-hole coupling is made at the selected one interface, and a steric hindrance is induced between the monomers of the remaining unselected interface.

22. An antibody and tumor necrosis factor superfamily (TNFSF) cytokine trimeric fusion protein produced according to the method of claim 20.

* * * * *

SEQUENCE LISTING

```
<160> NUMBER OF SEQ ID NOS: 35

<210> SEQ ID NO 1
<211> LENGTH: 169
<212> TYPE: PRT
<213> ORGANISM: Artificial
<220> FEATURE:
<223> OTHER INFORMATION: RACE-WT_Heavy chain I (monomer, WT)
```

```
<400> SEQUENCE: 1

Asp Lys Thr His Thr Cys Pro Pro Cys Pro Ala Pro Glu Leu Leu Gly
1               5                   10                  15

Gly Gly Met Phe Ala Gln Leu Val Ala Gln Asn Val Leu Leu Ile Asp
            20                  25                  30

Gly Pro Leu Ser Trp Tyr Ser Asp Pro Gly Leu Ala Gly Val Ser Leu
        35                  40                  45

Thr Gly Gly Leu Ser Tyr Lys Glu Asp Thr Lys Glu Leu Val Val Ala
    50                  55                  60

Lys Ala Gly Val Tyr Tyr Val Phe Phe Gln Leu Glu Leu Arg Arg Val
65                  70                  75                  80

Val Ala Gly Glu Gly Ser Gly Ser Val Ser Leu Ala Leu His Leu Gln
                85                  90                  95

Pro Leu Arg Ser Ala Ala Gly Ala Ala Ala Leu Ala Leu Thr Val Asp
            100                 105                 110

Leu Pro Pro Ala Ser Ser Glu Ala Arg Asn Ser Ala Phe Gly Phe Gln
        115                 120                 125

Gly Arg Leu Leu His Leu Ser Ala Gly Gln Arg Leu Gly Val His Leu
    130                 135                 140

His Thr Glu Ala Arg Ala Arg His Ala Trp Gln Leu Thr Gln Gly Ala
145                 150                 155                 160

Thr Val Leu Gly Leu Phe Arg Val Thr
                165

<210> SEQ ID NO 2
<211> LENGTH: 322
<212> TYPE: PRT
<213> ORGANISM: Artificial
<220> FEATURE:
<223> OTHER INFORMATION: RACE-WT_Heavy chain II (dimer, WT, G1 linker)

<400> SEQUENCE: 2

Asp Lys Thr His Thr Cys Pro Pro Cys Pro Ala Pro Glu Leu Leu Gly
1               5                   10                  15

Gly Gly Met Phe Ala Gln Leu Val Ala Gln Asn Val Leu Leu Ile Asp
            20                  25                  30

Gly Pro Leu Ser Trp Tyr Ser Asp Pro Gly Leu Ala Gly Val Ser Leu
        35                  40                  45

Thr Gly Gly Leu Ser Tyr Lys Glu Asp Thr Lys Glu Leu Val Val Ala
    50                  55                  60

Lys Ala Gly Val Tyr Tyr Val Phe Phe Gln Leu Glu Leu Arg Arg Val
65                  70                  75                  80

Val Ala Gly Glu Gly Ser Gly Ser Val Ser Leu Ala Leu His Leu Gln
                85                  90                  95

Pro Leu Arg Ser Ala Ala Gly Ala Ala Ala Leu Ala Leu Thr Val Asp
            100                 105                 110

Leu Pro Pro Ala Ser Ser Glu Ala Arg Asn Ser Ala Phe Gly Phe Gln
        115                 120                 125

Gly Arg Leu Leu His Leu Ser Ala Gly Gln Arg Leu Gly Val His Leu
    130                 135                 140

His Thr Glu Ala Arg Ala Arg His Ala Trp Gln Leu Thr Gln Gly Ala
145                 150                 155                 160

Thr Val Leu Gly Leu Phe Arg Val Thr Gly Gly Met Phe Ala Gln Leu
                165                 170                 175
```

```
Val Ala Gln Asn Val Leu Leu Ile Asp Gly Pro Leu Ser Trp Tyr Ser
            180                 185                 190

Asp Pro Gly Leu Ala Gly Val Ser Leu Thr Gly Gly Leu Ser Tyr Lys
        195                 200                 205

Glu Asp Thr Lys Glu Leu Val Val Ala Lys Ala Gly Val Tyr Tyr Val
    210                 215                 220

Phe Phe Gln Leu Glu Leu Arg Arg Val Val Ala Gly Glu Gly Ser Gly
225                 230                 235                 240

Ser Val Ser Leu Ala Leu His Leu Gln Pro Leu Arg Ser Ala Ala Gly
                245                 250                 255

Ala Ala Ala Leu Ala Leu Thr Val Asp Leu Pro Pro Ala Ser Ser Glu
            260                 265                 270

Ala Arg Asn Ser Ala Phe Gly Phe Gln Gly Arg Leu Leu His Leu Ser
        275                 280                 285

Ala Gly Gln Arg Leu Gly Val His Leu His Thr Glu Ala Arg Ala Arg
    290                 295                 300

His Ala Trp Gln Leu Thr Gln Gly Ala Thr Val Leu Gly Leu Phe Arg
305                 310                 315                 320

Val Thr

<210> SEQ ID NO 3
<211> LENGTH: 507
<212> TYPE: DNA
<213> ORGANISM: Artificial
<220> FEATURE:
<223> OTHER INFORMATION: RACE-WT_Heavy chain I (hinge + downstream,
      4-1BBL monomer)

<400> SEQUENCE: 3
gacaaaactc acacatgccc accgtgccca gcacctgaac tcctgggggg aggcatgttt      60
gcccagctgg tgcccagaa tgtgctgctg attgatggcc ctctgagctg gtacagcgat     120
cctggacttg ctggcgttag cctgactggc ggcctgagct acaaagagga caccaaagaa     180
ctggtggtgg ccaaggccgg cgtgtactac gtgttctttc agctggaact gcggagagtg     240
gtggccggcg aaggatctgg atctgtgtct ctggcactgc atctgcagcc tctgagatct     300
gctgctggtg cagctgccct ggctctgaca gttgatctgc ctcctgccag cagcgaggcc     360
agaaatagcg cctttggctt ccaaggcaga ctgctgcacc tgtctgctgg acagagactg     420
ggagtgcacc tccacacaga agccagagca agacacgcct ggcagctgac acaaggcgct     480
acagtgctgg gcctgttcag agtgaca                                        507

<210> SEQ ID NO 4
<211> LENGTH: 966
<212> TYPE: DNA
<213> ORGANISM: Artificial
<220> FEATURE:
<223> OTHER INFORMATION: RACE-WT_Heavy chain II (hinge + downstream,
      4-1BBL dimer)

<400> SEQUENCE: 4
gacaaaactc acacatgccc accgtgccca gcacctgaac tcctgggggg aggcatgttt      60
gcccagctgg tgcccagaa tgtgctgctg attgatggcc ctctgagctg gtacagcgat     120
cctggacttg ctggcgttag cctgactggc ggcctgagct acaaagagga caccaaagaa     180
ctggtggtgg ccaaggccgg cgtgtactac gtgttctttc agctggaact gcggagagtg     240
gtggccggcg aaggatctgg atctgtgtct ctggcactgc atctgcagcc tctgagatct     300
```

-continued

```
gctgctggtg cagctgccct ggctctgaca gttgatctgc ctcctgccag cagcgaggcc   360
agaaatagcg cctttggctt ccaaggcaga ctgctgcacc tgtctgctgg acagagactg   420
ggagtgcacc tccacacaga agccagagca agacacgcct ggcagctgac acaaggcgct   480
acagtgctgg gcctgttcag agtgacagga ggcatgtttg cccagctggt ggcccagaat   540
gtgctgctga ttgatggccc tctgagctgg tacagcgatc ctggacttgc tggcgttagc   600
ctgactggcg gcctgagcta caagaggac accaaagaac tggtggtggc caaggccggc   660
gtgtactacg tgttctttca gctggaactg cggagagtgg tggccggcga aggatctgga   720
tctgtgtctc tggcactgca tctgcagcct ctgagatctg ctgctggtgc agctgccctg   780
gctctgacag ttgatctgcc tcctgccagc agcgaggcca gaaatagcgc ctttggcttc   840
caaggcagac tgctgcacct gtctgctgga cagagactgg gagtgcacct ccacacagaa   900
gccagagcaa gacacgcctg gcagctgaca caaggcgcta cagtgctggg cctgttcaga   960
gtgaca                                                                966
```

<210> SEQ ID NO 5
<211> LENGTH: 169
<212> TYPE: PRT
<213> ORGANISM: Artificial
<220> FEATURE:
<223> OTHER INFORMATION: RACE-modified I_Heavy chain I (hinge + downstream, 4-1BBL monomer, R202W)

<400> SEQUENCE: 5

```
Asp Lys Thr His Thr Cys Pro Pro Cys Pro Ala Pro Glu Leu Leu Gly
 1               5                  10                  15
Gly Gly Met Phe Ala Gln Leu Val Ala Gln Asn Val Leu Leu Ile Asp
                20                  25                  30
Gly Pro Leu Ser Trp Tyr Ser Asp Pro Gly Leu Ala Gly Val Ser Leu
            35                  40                  45
Thr Gly Gly Leu Ser Tyr Lys Glu Asp Thr Lys Glu Leu Val Val Ala
        50                  55                  60
Lys Ala Gly Val Tyr Tyr Val Phe Phe Gln Leu Glu Leu Arg Arg Val
    65                  70                  75                  80
Val Ala Gly Glu Gly Ser Gly Ser Val Ser Leu Ala Leu His Leu Gln
                85                  90                  95
Pro Leu Arg Ser Ala Ala Gly Ala Ala Ala Leu Ala Leu Thr Val Asp
               100                 105                 110
Leu Pro Pro Ala Ser Ser Glu Ala Arg Asn Ser Ala Phe Gly Phe Gln
           115                 120                 125
Gly Arg Leu Leu His Leu Ser Ala Gly Gln Trp Leu Gly Val His Leu
       130                 135                 140
His Thr Glu Ala Arg Ala Arg His Ala Trp Gln Leu Thr Gln Gly Ala
145                 150                 155                 160
Thr Val Leu Gly Leu Phe Arg Val Thr
                165
```

<210> SEQ ID NO 6
<211> LENGTH: 322
<212> TYPE: PRT
<213> ORGANISM: Artificial
<220> FEATURE:
<223> OTHER INFORMATION: RACE-modified I_Heavy chain II (hinge + downstream, 4-1BBL dimer, Q94S, G1 linker)

<400> SEQUENCE: 6

```
Asp Lys Thr His Thr Cys Pro Pro Cys Pro Ala Pro Glu Leu Leu Gly
1               5                   10                  15

Gly Gly Met Phe Ala Ser Leu Val Ala Gln Asn Val Leu Leu Ile Asp
            20                  25                  30

Gly Pro Leu Ser Trp Tyr Ser Asp Pro Gly Leu Ala Gly Val Ser Leu
        35                  40                  45

Thr Gly Gly Leu Ser Tyr Lys Glu Asp Thr Lys Glu Leu Val Val Ala
    50                  55                  60

Lys Ala Gly Val Tyr Tyr Val Phe Phe Gln Leu Glu Leu Arg Arg Val
65                  70                  75                  80

Val Ala Gly Glu Gly Ser Gly Ser Val Ser Leu Ala Leu His Leu Gln
                85                  90                  95

Pro Leu Arg Ser Ala Ala Gly Ala Ala Ala Leu Ala Leu Thr Val Asp
            100                 105                 110

Leu Pro Pro Ala Ser Ser Glu Ala Arg Asn Ser Ala Phe Gly Phe Gln
        115                 120                 125

Gly Arg Leu Leu His Leu Ser Ala Gly Gln Arg Leu Gly Val His Leu
    130                 135                 140

His Thr Glu Ala Arg Ala Arg His Ala Trp Gln Leu Thr Gln Gly Ala
145                 150                 155                 160

Thr Val Leu Gly Leu Phe Arg Val Thr Gly Gly Met Phe Ala Gln Leu
                165                 170                 175

Val Ala Gln Asn Val Leu Leu Ile Asp Gly Pro Leu Ser Trp Tyr Ser
            180                 185                 190

Asp Pro Gly Leu Ala Gly Val Ser Leu Thr Gly Gly Leu Ser Tyr Lys
        195                 200                 205

Glu Asp Thr Lys Glu Leu Val Val Ala Lys Ala Gly Val Tyr Tyr Val
    210                 215                 220

Phe Phe Gln Leu Glu Leu Arg Arg Val Val Ala Gly Glu Gly Ser Gly
225                 230                 235                 240

Ser Val Ser Leu Ala Leu His Leu Gln Pro Leu Arg Ser Ala Ala Gly
                245                 250                 255

Ala Ala Ala Leu Ala Leu Thr Val Asp Leu Pro Pro Ala Ser Ser Glu
            260                 265                 270

Ala Arg Asn Ser Ala Phe Gly Phe Gln Gly Arg Leu Leu His Leu Ser
        275                 280                 285

Ala Gly Gln Arg Leu Gly Val His Leu His Thr Glu Ala Arg Ala Arg
    290                 295                 300

His Ala Trp Gln Leu Thr Gln Gly Ala Thr Val Leu Gly Leu Phe Arg
305                 310                 315                 320

Val Thr
```

<210> SEQ ID NO 7
<211> LENGTH: 507
<212> TYPE: DNA
<213> ORGANISM: Artificial
<220> FEATURE:
<223> OTHER INFORMATION: RACE-modified I_Heavy chain I (hinge + downstream, 4-1BBL monomer, R202W)

<400> SEQUENCE: 7

```
gacaaaactc acacatgccc accgtgccca gcacctgaac tcctgggggg aggcatgttt    60
gcccagctgg tggcccagaa tgtgctgctg attgatggcc ctctgagctg gtacagcgat   120
cctggacttg ctggcgttag cctgactggc ggcctgagct acaaagagga caccaaagaa   180
```

-continued

```
ctggtggtgg ccaaggccgg cgtgtactac gtgttctttc agctggaact gcggagagtg    240
gtggccggcg aaggatctgg atctgtgtct ctggcactgc atctgcagcc tctgagatct    300
gctgctggtg cagctgccct ggctctgaca gttgatctgc ctcctgccag cagcgaggcc    360
agaaatagcg cctttggctt ccaaggctgg ctgctgcacc tgtctgctgg acagagactg    420
ggagtgcacc tccacacaga agccagagca agacacgcct ggcagctgac acaaggcgct    480
acagtgctgg gcctgttcag agtgaca                                       507
```

<210> SEQ ID NO 8
<211> LENGTH: 966
<212> TYPE: DNA
<213> ORGANISM: Artificial
<220> FEATURE:
<223> OTHER INFORMATION: RACE-modified I_Heavy chain II (hinge + downstream, 4-1BBL dimer, Q94S, G1 linker)

<400> SEQUENCE: 8

```
gacaaaactc acacatgccc accgtgccca gcacctgaac tcctgggggg aggcatgttt     60
gccagcctgg tggcccagaa tgtgctgctg attgatggcc ctctgagctg gtacagcgat    120
cctggacttg ctggcgttag cctgactggc ggcctgagct acaaagagga caccaaagaa    180
ctggtggtgg ccaaggccgg cgtgtactac gtgttctttc agctggaact gcggagagtg    240
gtggccggcg aaggatctgg atctgtgtct ctggcactgc atctgcagcc tctgagatct    300
gctgctggtg cagctgccct ggctctgaca gttgatctgc ctcctgccag cagcgaggcc    360
agaaatagcg cctttggctt ccaaggcaga ctgctgcacc tgtctgctgg acagagactg    420
ggagtgcacc tccacacaga agccagagca agacacgcct ggcagctgac acaaggcgct    480
acagtgctgg gcctgttcag agtgacagga ggcatgtttg cccagctggt ggcccagaat    540
gtgctgctga ttgatggccc tctgagctgg tacagcgatc ctggacttgc tggcgttagc    600
ctgactggcg gcctgagcta caaagaggac accaaagaac tggtggtggc caaggccggc    660
gtgtactacg tgttctttca gctggaactg cggagagtgg tggccggcga aggatctgga    720
tctgtgtctc tggcactgca tctgcagcct ctgagatctg ctgctggtgc agctgccctg    780
gctctgacag ttgatctgcc tcctgccagc agcgaggcca gaaatagcgc ctttggcttc    840
caaggcagac tgctgcacct gtctgctgga cagagactgg gagtgcacct ccacacagaa    900
gccagagcaa gacacgcctg gcagctgaca caaggcgcta cagtgctggg cctgttcaga    960
gtgaca                                                              966
```

<210> SEQ ID NO 9
<211> LENGTH: 169
<212> TYPE: PRT
<213> ORGANISM: Artificial
<220> FEATURE:
<223> OTHER INFORMATION: RACE-modified II_Heavy chain I (hinge + downstream, 4-1BBL monomer, A180E)

<400> SEQUENCE: 9

```
Asp Lys Thr His Thr Cys Pro Pro Cys Pro Ala Pro Glu Leu Leu Gly
 1               5                  10                  15

Gly Gly Met Phe Ala Gln Leu Val Ala Gln Asn Val Leu Leu Ile Asp
            20                  25                  30

Gly Pro Leu Ser Trp Tyr Ser Asp Pro Gly Leu Ala Gly Val Ser Leu
        35                  40                  45

Thr Gly Gly Leu Ser Tyr Lys Glu Asp Thr Lys Glu Leu Val Val Ala
    50                  55                  60
```

```
Lys Ala Gly Val Tyr Tyr Val Phe Phe Gln Leu Glu Leu Arg Arg Val
 65                  70                  75                  80

Val Ala Gly Glu Gly Ser Gly Ser Val Ser Leu Ala Leu His Leu Gln
                 85                  90                  95

Pro Leu Arg Ser Ala Ala Gly Ala Ala Ala Leu Glu Leu Thr Val Asp
            100                 105                 110

Leu Pro Pro Ala Ser Ser Glu Ala Arg Asn Ser Ala Phe Gly Phe Gln
            115                 120                 125

Gly Arg Leu Leu His Leu Ser Ala Gly Gln Arg Leu Gly Val His Leu
        130                 135                 140

His Thr Glu Ala Arg Ala Arg His Ala Trp Gln Leu Thr Gln Gly Ala
145                 150                 155                 160

Thr Val Leu Gly Leu Phe Arg Val Thr
                165
```

<210> SEQ ID NO 10
<211> LENGTH: 322
<212> TYPE: PRT
<213> ORGANISM: Artificial
<220> FEATURE:
<223> OTHER INFORMATION: RACE-modified II_Heavy chain II (hinge +
      downstream, 4-1BBL dimer, E148G, G1 linker)

<400> SEQUENCE: 10

```
Asp Lys Thr His Thr Cys Pro Pro Cys Pro Ala Pro Glu Leu Leu Gly
 1               5                  10                  15

Gly Gly Met Phe Ala Gln Leu Val Ala Gln Asn Val Leu Leu Ile Asp
             20                  25                  30

Gly Pro Leu Ser Trp Tyr Ser Asp Pro Gly Leu Ala Gly Val Ser Leu
         35                  40                  45

Thr Gly Gly Leu Ser Tyr Lys Glu Asp Thr Lys Glu Leu Val Val Ala
 50                  55                  60

Lys Ala Gly Val Tyr Tyr Val Phe Phe Gln Leu Glu Leu Arg Arg Val
 65                  70                  75                  80

Val Ala Gly Glu Gly Ser Gly Ser Val Ser Leu Ala Leu His Leu Gln
                 85                  90                  95

Pro Leu Arg Ser Ala Ala Gly Ala Ala Ala Leu Ala Leu Thr Val Asp
            100                 105                 110

Leu Pro Pro Ala Ser Ser Glu Ala Arg Asn Ser Ala Phe Gly Phe Gln
            115                 120                 125

Gly Arg Leu Leu His Leu Ser Ala Gly Gln Arg Leu Gly Val His Leu
        130                 135                 140

His Thr Glu Ala Arg Ala Arg His Ala Trp Gln Leu Thr Gln Gly Ala
145                 150                 155                 160

Thr Val Leu Gly Leu Phe Arg Val Thr Gly Gly Met Phe Ala Gln Leu
                165                 170                 175

Val Ala Gln Asn Val Leu Leu Ile Asp Gly Pro Leu Ser Trp Tyr Ser
            180                 185                 190

Asp Pro Gly Leu Ala Gly Val Ser Leu Thr Gly Gly Leu Ser Tyr Lys
            195                 200                 205

Glu Asp Thr Lys Glu Leu Val Val Ala Lys Ala Gly Val Tyr Tyr Val
        210                 215                 220

Phe Phe Gln Leu Glu Leu Arg Arg Val Val Ala Gly Glu Gly Ser Gly
225                 230                 235                 240

Ser Val Ser Leu Ala Leu His Leu Gln Pro Leu Arg Ser Ala Ala Gly
```

Ala Ala Ala Leu Ala Leu Thr Val Asp Leu Pro Pro Ala Ser Ser Glu
            260                 265                 270

Ala Arg Asn Ser Ala Phe Gly Phe Gln Gly Arg Leu Leu His Leu Ser
        275                 280                 285

Ala Gly Gln Arg Leu Gly Val His Leu His Thr Glu Ala Arg Ala Arg
    290                 295                 300

His Ala Trp Gln Leu Thr Gln Gly Ala Thr Val Leu Gly Leu Phe Arg
305                 310                 315                 320

Val Thr

<210> SEQ ID NO 11
<211> LENGTH: 507
<212> TYPE: DNA
<213> ORGANISM: Artificial
<220> FEATURE:
<223> OTHER INFORMATION: RACE-modified II_Heavy chain I (hinge +
      downstream, 4-1BBL monomer, A180E)

<400> SEQUENCE: 11
gacaaaactc acacatgccc accgtgccca gcacctgaac tcctgggggg aggcatgttt     60
gcccagctgg tggcccagaa tgtgctgctg attgatggcc ctctgagctg gtacagcgat    120
cctggacttg ctggcgttag cctgactggc ggcctgagct acaaagagga caccaaagaa    180
ctggtggtgg ccaaggccgg cgtgtactac gtgttctttc agctggaact gcggagagtg    240
gtggccggcg aaggatctgg atctgtgtct ctggcactgc atctgcagcc tctgagatct    300
gctgctggtg cagctgccct ggaactgaca gttgatctgc ctcctgccag cagcgaggcc    360
agaaatagcg cctttggctt ccaaggctgg ctgctgcacc tgtctgctgg acagagactg    420
ggagtgcacc tccacacaga agccagagca agacacgcct ggcagctgac acaaggcgct    480
acagtgctgg gcctgttcag agtgaca                                       507

<210> SEQ ID NO 12
<211> LENGTH: 966
<212> TYPE: DNA
<213> ORGANISM: Artificial
<220> FEATURE:
<223> OTHER INFORMATION: RACE-modified II_Heavy chain II (hinge +
      downstream, 4-1BBL dimer, E148G, G1 linker)

<400> SEQUENCE: 12
gacaaaactc acacatgccc accgtgccca gcacctgaac tcctgggggg aggcatgttt     60
gccagcctgg tggcccagaa tgtgctgctg attgatggcc ctctgagctg gtacagcgat    120
cctggacttg ctggcgttag cctgactggc ggcctgagct acaaagagga caccaaagaa    180
ctggtggtgg ccaaggccgg cgtgtactac gtgttctttc agctgggact gcggagagtg    240
gtggccggcg aaggatctgg atctgtgtct ctggcactgc atctgcagcc tctgagatct    300
gctgctggtg cagctgccct ggctctgaca gttgatctgc ctcctgccag cagcgaggcc    360
agaaatagcg cctttggctt ccaaggcaga ctgctgcacc tgtctgctgg acagagactg    420
ggagtgcacc tccacacaga agccagagca agacacgcct ggcagctgac acaaggcgct    480
acagtgctgg gcctgttcag agtgacagga ggcatgtttg cccagctggt ggcccagaat    540
gtgctgctga ttgatggccc tctgagctgg tacagcgatc ctggacttgc tggcgttagc    600
ctgactggcg gcctgagcta caaagaggac accaaagaac tggtggtggc caaggccggc    660
gtgtactacg tgttctttca gctggaactg cggagagtgg tggccggcga aggatctgga    720

```
tctgtgtctc tggcactgca tctgcagcct ctgagatctg ctgctggtgc agctgccctg      780
gctctgacag ttgatctgcc tcctgccagc agcgaggcca gaaatagcgc ctttggcttc      840
caaggcagac tgctgcacct gtctgctgga cagagactgg gagtgcacct ccacacagaa      900
gccagagcaa gacacgcctg gcagctgaca caaggcgcta cagtgctggg cctgttcaga      960
gtgaca                                                                 966
```

<210> SEQ ID NO 13
<211> LENGTH: 169
<212> TYPE: PRT
<213> ORGANISM: Artificial
<220> FEATURE:
<223> OTHER INFORMATION: RACE-modified III_Heavy chain I (hinge + downstream, 4-1BBL monomer, V234R)

<400> SEQUENCE: 13

```
Asp Lys Thr His Thr Cys Pro Pro Cys Pro Ala Pro Glu Leu Leu Gly
1               5                   10                  15

Gly Gly Met Phe Ala Gln Leu Val Ala Gln Asn Val Leu Leu Ile Asp
            20                  25                  30

Gly Pro Leu Ser Trp Tyr Ser Asp Pro Gly Leu Ala Gly Val Ser Leu
        35                  40                  45

Thr Gly Gly Leu Ser Tyr Lys Glu Asp Thr Lys Glu Leu Val Val Ala
    50                  55                  60

Lys Ala Gly Val Tyr Tyr Val Phe Phe Gln Leu Glu Leu Arg Arg Val
65                  70                  75                  80

Val Ala Gly Glu Gly Ser Gly Ser Val Ser Leu Ala Leu His Leu Gln
                85                  90                  95

Pro Leu Arg Ser Ala Ala Gly Ala Ala Ala Leu Ala Leu Thr Val Asp
            100                 105                 110

Leu Pro Pro Ala Ser Ser Glu Ala Arg Asn Ser Ala Phe Gly Phe Gln
        115                 120                 125

Gly Arg Leu Leu His Leu Ser Ala Gly Gln Trp Leu Gly Val His Leu
    130                 135                 140

His Thr Glu Ala Arg Ala Arg His Ala Arg Gln Leu Thr Gln Gly Ala
145                 150                 155                 160

Thr Arg Leu Gly Leu Phe Arg Val Thr
                165
```

<210> SEQ ID NO 14
<211> LENGTH: 322
<212> TYPE: PRT
<213> ORGANISM: Artificial
<220> FEATURE:
<223> OTHER INFORMATION: RACE-modified III_Heavy chain II (hinge + downstream, 4-1BBL dimer, R202V, G1 linker)

<400> SEQUENCE: 14

```
Asp Lys Thr His Thr Cys Pro Pro Cys Pro Ala Pro Glu Leu Leu Gly
1               5                   10                  15

Gly Gly Met Phe Ala Gln Leu Val Ala Gln Asn Val Leu Leu Ile Asp
            20                  25                  30

Gly Pro Leu Ser Trp Tyr Ser Asp Pro Gly Leu Ala Gly Val Ser Leu
        35                  40                  45

Thr Gly Gly Leu Ser Tyr Lys Glu Asp Thr Lys Glu Leu Val Val Ala
    50                  55                  60

Lys Ala Gly Val Tyr Tyr Val Phe Phe Gln Leu Glu Leu Arg Arg Val
```

```
            65                  70                  75                  80
       Val Ala Gly Glu Gly Ser Gly Ser Val Ser Leu Ala Leu His Leu Gln
                            85                  90                  95

Pro Leu Arg Ser Ala Gly Ala Ala Leu Ala Leu Thr Val Asp
                       100                 105                 110

Leu Pro Pro Ala Ser Ser Glu Ala Arg Asn Ser Ala Phe Gly Phe Gln
                       115                 120                 125

Gly Arg Leu Leu His Leu Ser Ala Gly Gln Arg Leu Gly Val His Leu
                   130                 135                 140

His Thr Glu Ala Arg Ala Arg His Ala Trp Gln Leu Thr Gln Gly Ala
       145                 150                 155                 160

Thr Val Leu Gly Leu Phe Arg Val Thr Gly Gly Met Phe Ala Gln Leu
                           165                 170                 175

Val Ala Gln Asn Val Leu Leu Ile Asp Gly Pro Leu Ser Trp Tyr Ser
                       180                 185                 190

Asp Pro Gly Leu Ala Gly Val Ser Leu Thr Gly Gly Leu Ser Tyr Lys
                       195                 200                 205

Glu Asp Thr Lys Glu Leu Val Val Ala Lys Ala Gly Val Tyr Tyr Val
                   210                 215                 220

Phe Phe Gln Leu Glu Leu Arg Arg Val Val Ala Gly Glu Gly Ser Gly
       225                 230                 235                 240

Ser Val Ser Leu Ala Leu His Leu Gln Pro Leu Arg Ser Ala Ala Gly
                           245                 250                 255

Ala Ala Ala Leu Ala Leu Thr Val Asp Leu Pro Pro Ala Ser Ser Glu
                       260                 265                 270

Ala Arg Asn Ser Ala Phe Gly Phe Gln Gly Arg Leu Leu His Leu Ser
                       275                 280                 285

Ala Gly Gln Val Leu Gly Val His Leu His Thr Glu Ala Arg Ala Arg
                   290                 295                 300

His Ala Trp Gln Leu Thr Gln Gly Ala Thr Val Leu Gly Leu Phe Arg
       305                 310                 315                 320

Val Thr

<210> SEQ ID NO 15
<211> LENGTH: 507
<212> TYPE: DNA
<213> ORGANISM: Artificial
<220> FEATURE:
<223> OTHER INFORMATION: RACE-modified III_Heavy chain I (hinge +
      downstream, 4-1BBL monomer, V234R)

<400> SEQUENCE: 15
gacaaaactc acacatgccc accgtgccca gcacctgaac tcctgggggg aggcatgttt      60
gcccagctgg tggcccagaa tgtgctgctg attgatggcc ctctgagctg gtacagcgat     120
cctggacttg ctggcgttag cctgactggc ggcctgagct acaaagagga caccaaagaa     180
ctggtggtgg ccaaggccgg cgtgtactac gtgttctttc agctggaact gcggagagtg     240
gtggccggcg aaggatctgg atctgtgtct ctggcactgc atctgcagcc tctgagatct     300
gctgctggtg cagctgccct ggctctgaca gttgatctgc ctcctgccag cagcgaggcc     360
agaaatagcg cctttggctt ccaaggcaga ctgctgcacc tgtctgctgg acagagactg     420
ggagtgcacc tccacacaga agccagagca agacacgcct ggcagctgac acaaggcgct     480
acaagactgg gcctgttcag agtgaca                                         507
```

<210> SEQ ID NO 16
<211> LENGTH: 966
<212> TYPE: DNA
<213> ORGANISM: Artificial
<220> FEATURE:
<223> OTHER INFORMATION: RACE-modified III_Heavy chain II (hinge + downstream, 4-1BBL dimer, R202V, G1 linker)

<400> SEQUENCE: 16

```
gacaaaactc acacatgccc accgtgccca gcacctgaac tcctgggggg aggcatgttt      60
gcccagctgg tggcccagaa tgtgctgctg attgatggcc ctctgagctg gtacagcgat     120
cctggacttg ctggcgttag cctgactggc ggcctgagct acaaagagga caccaaagaa     180
ctggtggtgg ccaaggccgg cgtgtactac gtgttctttc agctggaact gcggagagtg     240
gtggccggcg aaggatctgg atctgtgtct ctggcactgc atctgcagcc tctgagatct     300
gctgctggtg cagctgccct ggctctgaca gttgatctgc ctcctgccag cagcgaggcc     360
agaaatagcg cctttggctt ccaaggcaga ctgctgcacc tgtctgctgg acagagactg     420
ggagtgcacc tccacacaga agccagagca agacacgcct ggcagctgac acaaggcgct     480
acagtgctgg gcctgttcag agtgacagga ggcatgtttg cccagctggt ggcccagaat     540
gtgctgctga ttgatggccc tctgagctgg tacagcgatc tggacttgc tggcgttagc      600
ctgactggcg gcctgagcta caaagaggac accaaagaac tggtggtggc caaggccggc     660
gtgtactacg tgttctttca gctggaactg cggagagtgg tggccggcga aggatctgga     720
tctgtgtctc tggcactgca tctgcagcct ctgagatctg ctgctggtgc agctgccctg     780
gctctgacag ttgatctgcc tcctgccagc agcgaggcca gaaatagcgc ctttggcttc     840
caaggcagac tgctgcacct gtctgctgga caggtgctgg gagtgcaccc ccacacagaa     900
gccagagcaa gacacgcctg gcagctgaca caaggcgcta cagtgctggg cctgttcaga     960
gtgaca                                                                966
```

<210> SEQ ID NO 17
<211> LENGTH: 152
<212> TYPE: PRT
<213> ORGANISM: Artificial
<220> FEATURE:
<223> OTHER INFORMATION: 4-1BBL

<400> SEQUENCE: 17

```
Gly Met Phe Ala Gln Leu Val Ala Gln Asn Val Leu Leu Ile Asp Gly
1               5                   10                  15

Pro Leu Ser Trp Tyr Ser Asp Pro Gly Leu Ala Gly Val Ser Leu Thr
            20                  25                  30

Gly Gly Leu Ser Tyr Lys Glu Asp Thr Lys Glu Leu Val Val Ala Lys
        35                  40                  45

Ala Gly Val Tyr Tyr Val Phe Phe Gln Leu Glu Leu Arg Arg Val Val
    50                  55                  60

Ala Gly Glu Gly Ser Gly Ser Val Ser Leu Ala Leu His Leu Gln Pro
65                  70                  75                  80

Leu Arg Ser Ala Ala Gly Ala Ala Ala Leu Ala Leu Thr Val Asp Leu
                85                  90                  95

Pro Pro Ala Ser Ser Glu Ala Arg Asn Ser Ala Phe Gly Phe Gln Gly
            100                 105                 110

Arg Leu Leu His Leu Ser Ala Gly Gln Arg Leu Gly Val His Leu His
        115                 120                 125

Thr Glu Ala Arg Ala Arg His Ala Trp Gln Leu Thr Gln Gly Ala Thr
```

```
                130                 135                 140
Val Leu Gly Leu Phe Arg Val Thr
145                 150
```

<210> SEQ ID NO 18
<211> LENGTH: 47
<212> TYPE: DNA
<213> ORGANISM: Artificial
<220> FEATURE:
<223> OTHER INFORMATION: Forward primer for First Fragment

<400> SEQUENCE: 18
tacacgtact tagtcgctga agctcttcta tgggatggag ctatatc                47

<210> SEQ ID NO 19
<211> LENGTH: 47
<212> TYPE: DNA
<213> ORGANISM: Artificial
<220> FEATURE:
<223> OTHER INFORMATION: Reverse primer for First Fragment

<400> SEQUENCE: 19
taggtacgaa ctcgattgac ggctcttcat cccccagga gttcagg                 47

<210> SEQ ID NO 20
<211> LENGTH: 48
<212> TYPE: DNA
<213> ORGANISM: Artificial
<220> FEATURE:
<223> OTHER INFORMATION: Forward primer for Second Fragment

<400> SEQUENCE: 20
tacacgtact tagtcgctga agctcttcag gaggcatgtt tgcccagc               48

<210> SEQ ID NO 21
<211> LENGTH: 53
<212> TYPE: DNA
<213> ORGANISM: Artificial
<220> FEATURE:
<223> OTHER INFORMATION: Reverse primer for Second Fragment

<400> SEQUENCE: 21
taggtacgaa ctcgattgac ggctcttcag cctcctgtca ctctgaacag gcc         53

<210> SEQ ID NO 22
<211> LENGTH: 45
<212> TYPE: DNA
<213> ORGANISM: Artificial
<220> FEATURE:
<223> OTHER INFORMATION: Forward primer for Third Fragment

<400> SEQUENCE: 22
tacacgtact tagtcgctga agctcttcag gcatgtttgc ccagc                  45

<210> SEQ ID NO 23
<211> LENGTH: 52
<212> TYPE: DNA
<213> ORGANISM: Artificial
<220> FEATURE:
<223> OTHER INFORMATION: Reverse primer for Third Fragment

<400> SEQUENCE: 23
aggtacgaac tcgattgacg gctcttcaga gttatgtcac tctgaacagg cc          52

<210> SEQ ID NO 24

```
<211> LENGTH: 47
<212> TYPE: DNA
<213> ORGANISM: Artificial
<220> FEATURE:
<223> OTHER INFORMATION: Forward primer for First Fragment

<400> SEQUENCE: 24
tacacgtact tagtcgctga agctcttcta tgggatggag ctatatc          47

<210> SEQ ID NO 25
<211> LENGTH: 46
<212> TYPE: DNA
<213> ORGANISM: Artificial
<220> FEATURE:
<223> OTHER INFORMATION: Reverse primer for First Fragment

<400> SEQUENCE: 25
taggtacgaa ctcgattgac ggctcttatc cccccaggag ttcagg           46

<210> SEQ ID NO 26
<211> LENGTH: 48
<212> TYPE: DNA
<213> ORGANISM: Artificial
<220> FEATURE:
<223> OTHER INFORMATION: Forward primer for Second Fragment

<400> SEQUENCE: 26
tacacgtact tagtcgctga agctcttcag gaggcatgtt tgcccagc         48

<210> SEQ ID NO 27
<211> LENGTH: 52
<212> TYPE: DNA
<213> ORGANISM: Artificial
<220> FEATURE:
<223> OTHER INFORMATION: Reverse primer for Second Fragment

<400> SEQUENCE: 27
aggtacgaac tcgattgacg gctcttcaga gttatgtcac tctgaacagg cc    52

<210> SEQ ID NO 28
<211> LENGTH: 47
<212> TYPE: DNA
<213> ORGANISM: Artificial
<220> FEATURE:
<223> OTHER INFORMATION: Forward primer for single Fragment

<400> SEQUENCE: 28
tacacgtact tagtcgctga agctcttcta gatctgtggc tgcacca          47

<210> SEQ ID NO 29
<211> LENGTH: 46
<212> TYPE: DNA
<213> ORGANISM: Artificial
<220> FEATURE:
<223> OTHER INFORMATION: Reverse primer for single Fragment

<400> SEQUENCE: 29
aggtacgaac tcgattgacg gctcttcatc tcttcacttc cacctt           46

<210> SEQ ID NO 30
<211> LENGTH: 48
<212> TYPE: DNA
<213> ORGANISM: Artificial
<220> FEATURE:
<223> OTHER INFORMATION: Forward primer for dimer(Q94S)

<400> SEQUENCE: 30
```
tacacgtact tagtcgctga agctcttcta gcctggtggc ccagaatg    48

<210> SEQ ID NO 31
<211> LENGTH: 47
<212> TYPE: DNA
<213> ORGANISM: Artificial
<220> FEATURE:
<223> OTHER INFORMATION: Reverse primer for dimer(Q94S)

<400> SEQUENCE: 31
taggtacgaa ctcgattgac ggctcttcag ctggcaaaca tgcctcc    47

<210> SEQ ID NO 32
<211> LENGTH: 48
<212> TYPE: DNA
<213> ORGANISM: Artificial
<220> FEATURE:
<223> OTHER INFORMATION: Forward primer for Monomer(R202W)

<400> SEQUENCE: 32
tacacgtact tagtcgctga agctcttctt ggctgctgca cctgtctg    48

<210> SEQ ID NO 33
<211> LENGTH: 47
<212> TYPE: DNA
<213> ORGANISM: Artificial
<220> FEATURE:
<223> OTHER INFORMATION: Reverse primer for Monomer(R202W)

<400> SEQUENCE: 33
gtacgaactc gattgacggc tcttcaccag ccttggaagc caaaggc    47

<210> SEQ ID NO 34
<211> LENGTH: 5
<212> TYPE: PRT
<213> ORGANISM: Artificial
<220> FEATURE:
<223> OTHER INFORMATION: Linker

<400> SEQUENCE: 34

Gly Gly Gly Gly Ser
1               5

<210> SEQ ID NO 35
<211> LENGTH: 254
<212> TYPE: PRT
<213> ORGANISM: Homo sapiens

<400> SEQUENCE: 35

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
        50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp

-continued

```
                    100                 105                 110
Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
        130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
            195                 200                 205

Gly Gln Arg Leu Gly Val His Leu His Thr Glu Ala Arg Ala Arg His
            210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```